United States Patent
Geddes

(10) Patent No.: US 9,459,212 B2
(45) Date of Patent: *Oct. 4, 2016

(54) MIXED-METAL SUBSTRATES FOR METAL-ENHANCED FLUORESCENCE

(75) Inventor: Chris D. Geddes, Bel-Air, MD (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/516,103

(22) PCT Filed: Dec. 17, 2010

(86) PCT No.: PCT/US2010/060958
§ 371 (c)(1),
(2), (4) Date: Jul. 27, 2012

(87) PCT Pub. No.: WO2011/084671
PCT Pub. Date: Jul. 14, 2011

(65) Prior Publication Data
US 2012/0282630 A1    Nov. 8, 2012

Related U.S. Application Data

(60) Provisional application No. 61/287,314, filed on Dec. 17, 2009.

(51) Int. Cl.
| | |
|---|---|
| G01N 21/64 | (2006.01) |
| G01N 21/55 | (2014.01) |
| G01N 33/553 | (2006.01) |
| G01N 33/58 | (2006.01) |
| G01N 33/543 | (2006.01) |
| G01N 21/552 | (2014.01) |
| B82Y 15/00 | (2011.01) |

(52) U.S. Cl.
CPC .......... G01N 21/648 (2013.01); G01N 21/554 (2013.01); G01N 33/54346 (2013.01); G01N 33/553 (2013.01); G01N 33/582 (2013.01); B82Y 15/00 (2013.01)

(58) Field of Classification Search
None
See application file for complete search history.

(56) References Cited

U.S. PATENT DOCUMENTS 3,979,184 A * 9/1976 Giaever .................. 422/429
4,054,646 A * 10/1977 Giaever .................. 435/5
(Continued)

FOREIGN PATENT DOCUMENTS

WO    WO 2004024191    3/2004

OTHER PUBLICATIONS

Lal, S. et al., "Tailoring plasmonic substrates for surface enhanced spectroscopies", Chemical Society Reviews (2008) 37:898-911.*
(Continued)

Primary Examiner — Erik B Crawford
Assistant Examiner — Gary E Hollinden
(74) Attorney, Agent, or Firm — Marianne Fuierer; Moore & Van Allen, PLLC

(57) ABSTRACT

The present invention provides for mixed metal structures that can be deposited on a substrate or free in solution that exhibit several distinctive properties including a broad wavelength range for enhancing fluorescence signatures. Further, metal surface plasmons can couple and such diphase coupled luminescence signatures create extra plasmon absorption bands. The extra bands allow for a broad range of fluorophores to couple therefore making more generic substrates with wider reaching applications.

5 Claims, 24 Drawing Sheets

(56) References Cited

U.S. PATENT DOCUMENTS

| | | | |
|---|---|---|---|
| 4,092,116 A * | 5/1978 | Giaever | 435/5 |
| 5,017,009 A | 5/1991 | Schutt et al. | |
| 5,384,265 A * | 1/1995 | Kidwell et al. | 436/525 |
| 5,449,918 A | 9/1995 | Krull et al. | |
| 5,841,143 A | 11/1998 | Tuma et al. | |
| 5,866,433 A | 2/1999 | Schalkhammer et al. | |
| 6,699,724 B1 * | 3/2004 | West et al. | 436/525 |
| 6,818,199 B1 * | 11/2004 | Hainfeld et al. | 424/1.11 |
| 6,855,551 B2 * | 2/2005 | Bawendi et al. | 436/6 |
| 7,095,502 B2 | 8/2006 | Lakowicz et al. | |
| 7,253,452 B2 | 8/2007 | Steckel et al. | |
| 7,348,182 B2 | 3/2008 | Martin et al. | |
| 7,351,590 B2 | 4/2008 | Martin | |
| 7,400,397 B2 | 7/2008 | Lakowicz et al. | |
| 7,566,783 B2 | 7/2009 | Lakowicz | |
| 7,648,834 B2 | 1/2010 | Moore | |
| 7,718,445 B2 | 5/2010 | Martin | |
| 7,718,804 B2 | 5/2010 | Geddes et al. | |
| 7,732,215 B2 | 6/2010 | Geddes et al. | |
| 7,939,333 B2 | 5/2011 | Geddes et al. | |
| 7,989,220 B2 | 8/2011 | Lakowicz et al. | |
| 8,008,067 B2 | 8/2011 | Geddes et al. | |
| 8,027,039 B2 | 9/2011 | Lakowicz et al. | |
| 8,034,633 B2 | 10/2011 | Geddes | |
| 8,075,956 B2 | 12/2011 | Geddes et al. | |
| 8,088,631 B2 * | 1/2012 | Capobianco et al. | 436/525 |
| 8,101,424 B2 | 1/2012 | Geddes | |
| 8,114,598 B2 | 2/2012 | Geddes et al. | |
| 8,182,878 B2 | 5/2012 | Geddes et al. | |
| 8,318,087 B2 | 11/2012 | Geddes | |
| 8,338,602 B2 | 12/2012 | Geddes et al. | |
| 8,404,450 B2 | 3/2013 | Geddes et al. | |
| 8,481,335 B2 * | 7/2013 | Shih et al. | 436/524 |
| 8,497,131 B2 * | 7/2013 | Natan et al. | 436/56 |
| 8,802,447 B2 * | 8/2014 | Swager et al. | 436/528 |
| 8,835,185 B2 * | 9/2014 | Nishiuma et al. | 436/525 |
| 2001/0053521 A1 * | 12/2001 | Kreimer et al. | 435/6 |
| 2003/0157732 A1 * | 8/2003 | Baker et al. | 436/531 |
| 2003/0228682 A1 * | 12/2003 | Lakowicz et al. | 435/287.2 |
| 2004/0002089 A1 * | 1/2004 | Dubertret et al. | 435/6 |
| 2005/0053974 A1 * | 3/2005 | Lakowicz et al. | 435/6 |
| 2005/0064604 A1 * | 3/2005 | Bohmann et al. | 436/525 |
| 2006/0034729 A1 * | 2/2006 | Poponin | 422/82.05 |
| 2007/0117151 A1 * | 5/2007 | Frederix et al. | 435/7.1 |
| 2007/0166761 A1 * | 7/2007 | Moore | 435/7.1 |
| 2007/0269826 A1 | 11/2007 | Geddes et al. | |
| 2008/0215122 A1 | 9/2008 | Geddes et al. | |
| 2009/0022766 A1 | 1/2009 | Geddes et al. | |
| 2009/0023202 A1 | 1/2009 | Narahara et al. | |
| 2009/0069193 A1 * | 3/2009 | Flemming et al. | 506/9 |
| 2009/0118605 A1 * | 5/2009 | Van Duyne et al. | 600/365 |
| 2009/0325199 A1 | 12/2009 | Geddes et al. | |
| 2010/0062545 A1 | 3/2010 | Geddes et al. | |
| 2010/0149540 A1 * | 6/2010 | Boukherroub et al. | 356/445 |
| 2010/0209937 A1 | 8/2010 | Geddes et al. | |
| 2010/0297016 A1 | 11/2010 | Geddes et al. | |
| 2010/0311103 A1 * | 12/2010 | Boukherroub et al. | 435/29 |
| 2011/0020946 A1 | 1/2011 | Geddes | |
| 2011/0124117 A1 * | 5/2011 | Doering et al. | 436/501 |
| 2011/0136154 A1 | 6/2011 | Geddes | |
| 2011/0207236 A1 | 8/2011 | Geddes | |
| 2012/0021443 A1 | 1/2012 | Geddes | |
| 2012/0028270 A1 | 2/2012 | Geddes | |
| 2012/0091349 A1 | 4/2012 | Geddes | |
| 2012/0107952 A1 | 5/2012 | Geddes et al. | |
| 2012/0122240 A1 | 5/2012 | Geddes | |
| 2013/0020503 A1 | 1/2013 | Geddes | |
| 2013/0059316 A1 | 3/2013 | Geddes | |

OTHER PUBLICATIONS

Wei, Q.H. et al., "Engineering 'hot spots' fo surface enhanced raman scattering", Proceedings of SPIE (2003) 5221:92-99.*

Haynes, C.L. et al., "Nanosphere lithography: a versatile nanofbriacation tool for studies of size-dependent nanoparticle optics", J. Phys. Chem. B (2001) 105:5599-5611.*

Aslan, Kadir et al. Metal-enhanced fluorescence: an emerging tool in biotechnology, Current Opinion in Biotechnology (2005) 16, 55-62.

Aslan, Kadir et al. Angular-dependent metal-enhanced fluorescence from silver island films, Chemical Physics Letters (2008) 453, 222-228.

Aslan, Kadir et al. Extraction and detection of DNA from Bacillus anthracis spores and the vegetative cells within 1 min, Analytical Chemistry (2008) 80, 4125-4132.

Chowdhury, Sanchair et al. Silver-copper alloy nanoparticles for metal enhanced luminescence. (2009) Applied Physics Letters 95.

Chowdhury, Mustafa H. et al. Aluminum nanoparticles as substrates for metal-enhanced fluorescence in the ultraviolet for the label-free detection of biomolecules, Anal. Chem. (2009) 81, 1397-1403.

Chowdhury, Mustafa H. et al. Metal-enhanced chemiluminescence, Journal of Fluorescence (2006) 16, 295-299.

D'Agostino, Stefania et al. Enhanced fluorescence by metal nanospheres on metal substrates, Opt. Lett. (2009) 34, 2381-2383.

Dragan, A. I. et al. Metal-enhanced PicoGreen fluorescence: Application for double-stranded DNA quantification, Anal. Biochem. (2010) 396, 8-12.

Dragan, A. I. et al. Indium nanodeposits: A substrate for Metal-Enhanced Fluorescence in the UV spectral region, Journal of Applied Physics (2010) 108, .094701.

Dragan, A. I. et al. Distance dependence of metal-enhanced fluorescence, Plasmonics (2012) 7:739-744.

Dragan, A. I. et al. Excitation Volumetric Effects (EVE) in Metal-Enhanced Fluorescence., Phys, Chem. Chem. Phys. (2011) 13, 3831-3838.

Drexhage, K. H. Influence of a dielectric interface on fluorescence decay time., J. Lumin 1, (1970) 693-701.

Geddes, Chris D. et al. Metal-enhanced fluorescence, Journal of Fluorescence 12, (2002) 121-129.

Hirayama, Kazuo et al. Rapid confirmation and revision of the primary structure of bovine serum albumin by ESIMS and Frit-FAB LC/MS, Biochem. Biophys. Res. Commun. (1990) 173, 639-646.

Mackowski, Sebastian et al. Metal-enhanced fluorescence of chlorophylls in single light-harvesting complexes, Nano. Lett. 8 (2008) 558-564.

Matveeva, Evgenia G. et al. Metal particle-enhanced fluorescent immunoassays on metal mirrors, Analytical Biochemistry 363, (2007) 239-245.

Nooney, R.I. et al. Optimization of plasmonic enhancement of fluorescence on plastic substrates. Langmuir. Sep. 5, 2008 24(19):11261-7.

Persson, B. N. J. Theory of dumping of excited molecules located above a metalic-surface., J. Phys. C Solid State Phys (1978) 4251-4269.

Phan, T. G. et al. Practical intravital two-photon microscopy for immunological research: faster, brighter, deeper, Immunology and Cell Biology (2010) 88, 438-444.

Pribik, R. et al. Metal-Enhanced Fluorescence (MEF): Physical characterization of Silver-island films and exploring sample geometries, Chemical Physics Letters (2009) 478, 70-74.

Ray, Krishanu et al. Distance-dependent metal-enhanced fluorescence from Langmuir-Blodgett monolayers of alkyl-NBD derivatives on silver island films, Langmuir (2006) 22, 8374-8378.

Wang, Hui et al. Plasmonic nanostructures: Artificial molecules, Accounts of Chemical Research (2007) 40, 53-62.

Zhang, Yongxia et al. Metal-enhanced phosphorescence: Interpretation in terms of triplet-coupled radiating plasmons, Journal of Physical Chemistry B (2006)110, 25108-25114.

Zhang, Yongxia et al. Metal-enhanced singlet oxygen generation: A consequence of plasmon enhanced triplet yields, Journal of Fluorescence (2007) 17, 345-349.

Zhang, Yongxia et al. Metal-enhanced superoxide generation: A consequence of plasmon-enhanced triplet yields, Applied Physics Letters (2007) 91, 023114.

Zhang, Yongxia et al. Wavelength Dependence of Metal-Enhanced Fluorescence, Journal of Physical Chemistry C (2009) 113, 12095-12100.

Zhang, Yongxia et al. Metal-enhanced fluorescence from silver-SiO2-silver nanoburger structures, Langmuir (2010) 26, 12371-12376.

* cited by examiner

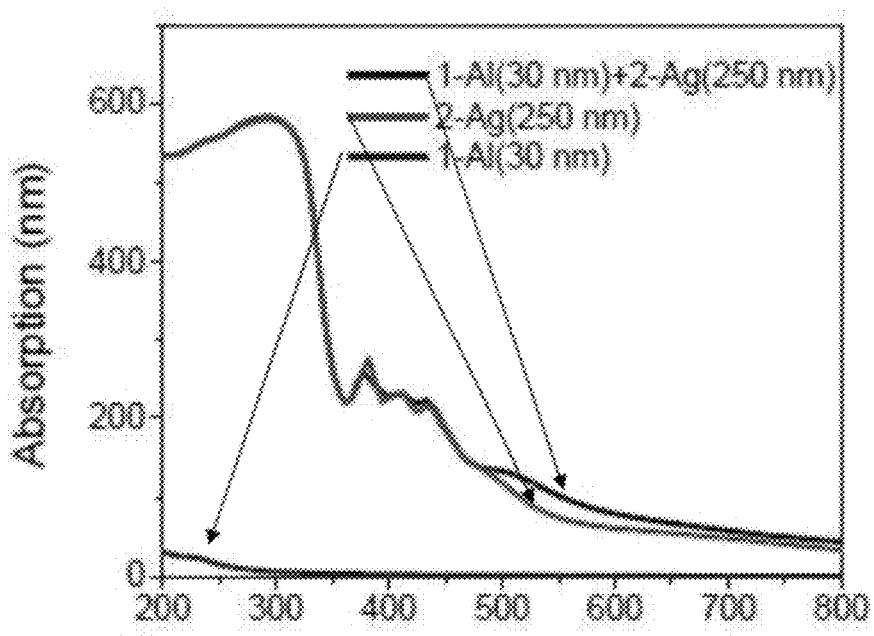
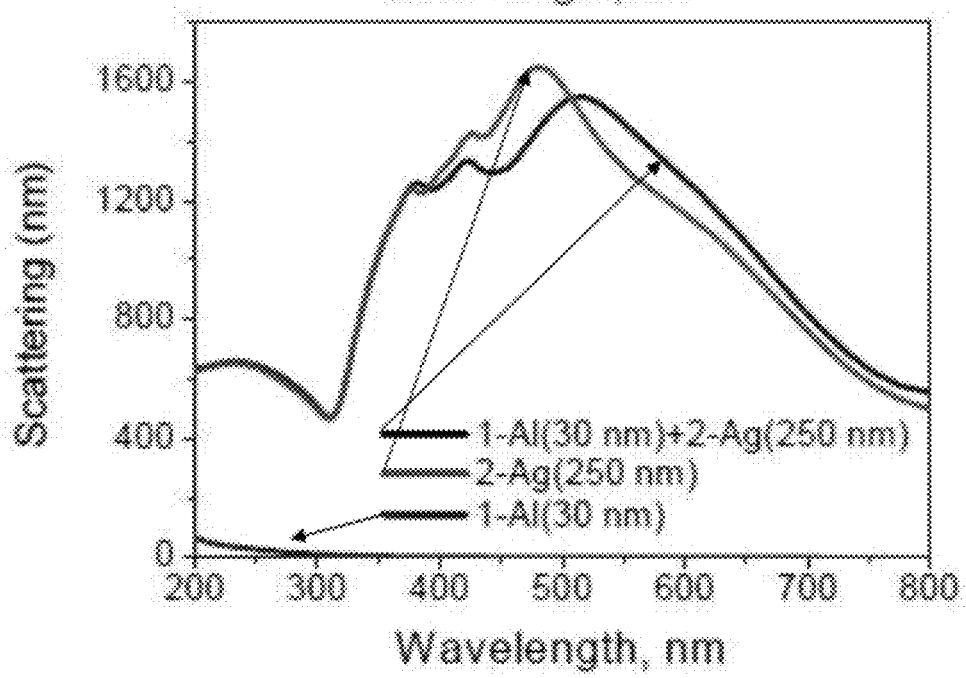
Figure 7B and C

MIXED-METAL SUBSTRATES FOR METAL-ENHANCED FLUORESCENCE

CROSS-REFERENCE TO RELATED APPLICATIONS

This application is a 35 U.S.C. §371 application of International Patent Application No. PCT/US2010/060958 filed on Dec. 17, 2010 which in turn claims priority to U.S. Provisional Patent Application No. 61/287,314 filed on Dec. 17, 2009, the content of which is hereby incorporated by reference herein for all purposes.

BACKGROUND OF THE INVENTION

1. Field of the Invention

The present invention relates to metallic structures, and more particularly, to mixed-metal structures for use in metal enhanced emission systems to enhance emissions from fluorophores, luminophores, bioluminescent species, chemiluminescent species and light emitting devices.

2. Background of the Related Art

In the last decade the interaction of fluorophores with metallic nano-particles has attracted significant literature (1-5), with numerous applications focused at the life sciences (2, 6-9). Fluorophore near-field interactions with plasmon supporting materials typically leads to enhanced fluorescence signatures (3, 5, 10, 11), and reduced fluorophore lifetimes, which, invariably lends itself to enhanced fluorophore photostabilities. Enhanced Chemiluminescence signatures (12), as well as enhanced triplet yields have also been reported from different metallic surfaces (13), with enhanced triplet yields giving rise to a variety of favorable reactive oxygen photophysics, such as enhanced singlet oxygen and superoxide anion radical generation (14, 15). The wavelength dependence of metal enhanced fluorescence (MEF) has also recently been postulated (16), as well as the angular dependence of emission (17), the distance dependence of MEF (18, 19), as well as excitation volumetric effects (EVE) (20), which readily allows for tunable luminescence enhancement factors. Since MEF was defined nearly a decade ago (3) and the mechanism postulated only a few years later (21), nearly all the reports of MEF have involved the exclusive use of single metallic substrates. Several reports of mixed metal continuous film coatings for SPCF and particularly substrates utilizing dielectric coatings or spacer layers e.g. $SiO_2$ and $SiO_x$, can be found in the research literature (22, 23). There is also a significant literature on the plasmonics properties of metal-metal coatings, such as Halas et al (24, 25), although none of these reports involve near-field dipoles and enhanced fluorescence signatures.

Notably, these studies have been focused on one single metal structure including a single metal such as Silver Island Films (SiFs) and provide no ability to provide mixed metal structures that can be used to enhance fluorescence as compared to the individual metal substrates alone. Thus it would advantageous to provide metallic particles that include mixed metals to provide increased intensity of fluorescence and photostability.

SUMMARY OF THE INVENTION

The present invention provides for mixed metal structures that can be deposited on a substrate or free in solution that exhibit several distinctive properties including; a broad wavelength range for enhancing fluorescence signatures and luminescence intensities. Further, the presence of two metals creates a new dephased plasmon resonance band, not evident in the optical properties of each individual metal. Still further, metal surface plasmons can couple and such diphase coupled luminescence signatures create extra plasmon absorption bands. The extra bands allow for a broad range of fluorophores to couple therefore making more generic substrates with wider reaching applications. In addition, a much more pronounced photostability is observed for fluorophores near-to mixed metals as compared to virgin metals.

The mixed metal structures can be used for fluorescence, phosphorescence and chemiluminescence signatures and a range of organic and inorganic chromophores, including quantum dots, GFP, semi-conductor emitters and silica nanoparticles. The mixed-metal structures provide for significantly enhanced intensity of fluorescence, decreased lifetime and increased luminophore photostability. The metallic structures may be fabricated from a combination of at least two metals selected from the group consisting of Silver, Gold, Aluminium, Zinc, Rhodium, Copper, Nickel, Palladium, Indium, Tin, Iron, Tungsten, Platinum and Germanium. The mixed metals are mixed, as either a homogeneous mixture or hetergeneous mixture, or in the alternative may be layered. Yet further advantages include the ability of some sensitive metals to be protected from other metals by using metals with different chemical properties. For example, gold capped silver could be used to enhance fluorescence, but also protect the silver from long term oxidation.

The mixed metal structure can be used to develop surfaces spanning broad wavelength ranges and can be used to change the reflective and/or absorption properties of metalized substrates, yet still provide for enhanced luminescence signatures.

The mixed metal-substrates can be used to tune the enhancement factor of specific wavelength fluorophores and generate enhanced plasmonics electricity ranges, not achievable by using a single metal.

In one aspect the present invention provides a substrate comprising non-connecting metalized structures that are spatially separated, wherein the metalized structures comprise mixed-metal layers with a dielectric material, such as a metal oxide layer positioned therebetween. Further, the structures may include one layer of a single metal, an oxide layer and another metal layer of a different metal wherein the oxide layer is positioned between the metal layers.

In another aspect, the mixed metal structures may can be fabricated to form a geometric shape such as triangle, square, oblong, elliptical, rectangle, or any shape that provides at least one apex area of the metallic surface. It is envisioned that the apex area includes not only pointed regions but regions with rounded edges such as found in an oblong or elliptical shape. The apex areas are preferably arranged so that one apex area is opposite from another apex area and aligned to form a reactive zone to be positioned therebetween. The distances between the apex areas may range from 0.01 mm to 5 mm, more preferably from 2 mm to about 3 mm. The thickness of the metallic geometric shaped forms ranges from 10 nm to about 1000 nm, and more preferably from about 45 nm to about 250 nm.

The metallic structures may include a combination of metals, deposited in any order on a substrate, for example silver, gold, or gold and then a silver layer. Further, the metallic structures can be in a nanoball shape with an internal metal core, a silica or oxide layer and another top metallic layer wherein the core metal is different from the outer layer. In the alternative, both the core and outer layers may be fabricated of a mixed-metal combination.

In one aspect, the present invention provides for a detection system, the system comprising:
- a) a substrate comprising a multiplicity of metallic structures, wherein the metallic structures comprise mixed-metals;
- b) at least one excitable molecule that is positioned near the metallic structure material in a range from about 5 nm to 50 nm, wherein the excitable molecule is selected from the group of an intrinsic fluorophore, extrinsic fluorophore, fluorescent dye, and luminophores;
- c) a source of electromagnetic energy for providing excitation energy to excite the molecule; and
- d) a detector for detecting emissions from the excited molecule and/or the metallic structure.

The emission enhancement may be observed when the fluorophores or luminophores are positioned from about 5 nm to about 200 nm to metal surfaces. Preferable distances are about 5 nm to about 30 nm, and more preferably, 5 nm to about 20 nm to metal surfaces.

Another aspect of the invention relates to a method of enhancing emissions from fluorescence, chemiluminescence, bioluminescence, and luminescence molecules and reactions that exhibit emissions in wavelengths from UV-visible to near IR.

The present invention relates to a method of detection using plasmonic emissions from metallic surfaces caused by fluorescence, chemiluminescence or bioluminescence based reactions. These plasmonic emissions emitted from metallic surface plasmons are generated either with an external excitation or without such external excitation due to chemically induced electronically excited states. Further, the mixed metal structures may be used to enhance spectral regions were the metals themselves do not have plasmon resonance, due to the creation of new mixed metal plasmon bands.

In yet another aspect, the present invention relates to a method of metal-enhanced fluorescence sensing, comprising:
- a) applying mixed metallic structures to a surface used in a detection system;
- b) introducing a solution containing at least one biomolecule for disposing near the metallic structures, wherein the biomolecule is capable of a chemically induced electronically excited state;
- c) triggering the chemically induced electronically excited state of the biomolecule; and
- d) measuring the bioluminescent or chemiluminescent intensity.

In yet another aspect, the present invention relates to a method for detecting a target molecule in a sample, the method comprising:
- a) providing a system comprising:
  - i) a layer of immobilized metallic structures comprising mixed metal, wherein the immobilized metallic structures have attached thereto a capture biomolecular probe with an affinity for the target molecule; and ii) a free biomolecular probe with an affinity for the target molecule, wherein the free biomolecular probe has attached thereto a fluorophore;
- b) contacting the sample with the immobilized metallic structures and capture biomolecular probes, wherein the target molecules binds to the capture biomolecular probes; and
- c) contacting the bound target molecule with the free biomolecular probe, wherein binding of the free biomolecular probe to the target molecule causes the fluorophore to be positioned a sufficient distance from the immobilized metallic structures to enhance fluorescence emission when excited by an irradiating source.

The substrate positioned beneath the metallic structures may include glass, quartz, plastics (such as on the bottom of HTS plates, polystyrene, polycarbonate), semiconductors, paper, cellulose, cotton, nylon, silk, very thin metal sheets, sapphire, diamond, ruby, dielectric materials, such as polystyrene etc.

An oxide layer, positioned between two mixed metal layers, may be formed from a deposition technique, such as vapor deposition. The oxide layer coating may include at least one metal selected from the group consisting of Al, Ti, Fe, Cu, Zn, Y, Zr, Nb, Mo, In, Si, Sn, Sb, Ta, W, Pb, Bi and Ce and having a valence of from 2 to 6. The form of the oxide of such a metal may, for example, be $Al_2O_3$, $SiO_2$, $TiO_2$, $Fe_2O_3$, $CuO$, $ZnO$, $Y_2O_3$, $ZrO_2$, $Nb_2O_5$, $MoO_3$, $In_2O_3$, $SnO_2$, $Sb_2O_5$, $Ta_2O_5$, $WO_3$, $PbO$ or $Bi_2O_3$. These metal oxides may be used alone or in combination with other types of coatings. Preferably, the oxide is a silicon oxide, more preferably, $SiO_2$. The vapor deposition of $SiO_2$ is a well established technique for the controlled deposition of a variety of substrates. For example, an Edwards Vapor deposition module allows the deposition of an inert coating of $SiO_2$, Further, a dielectric layer may include $MgF_2$ or $CaF_2$.

A still further aspect of the invention relates to a bioassay for measuring concentration of receptor-ligand binding in a test sample, the method comprising:
- a) preparing mixed metal structures of the present invention immobilized on a surface wherein the mixed metal structures have positioned thereon a receptor molecule having affinity for a ligand of interest;
- b) contacting the receptor molecule with the test sample suspected of comprising the ligand of interest, wherein the ligand of interest will bind to the receptor molecule to form a receptor-ligand complex;
- c) contacting the receptor-ligand complex with a detector molecule having affinity for the ligand to form a receptor-ligand-detector complex, wherein the detector molecule comprises a first component of a bioluminescence or chemiluminescence generating system;
- d) exposing the first component of the bioluminescence or chemiluminescence generating system to a trigger solution comprising a second component that will chemically react with the first component to induce a chemically electronically excited state; and
- e) measuring the intensity of radiation emitted from exited metallic surface plasmons and/or test sample.

Preferably, the components of the bioluminescence generating system are a luciferase and a luciferin. The bioluminescence generating system may be selected from the group consisting of those isolated from the ctenophores, coelenterases, mollusca, fish, ostracods, insects, bacteria, a crustacea, annelids, and earthworms. The luciferase may be selected from the group consisting of *Aequorea, Vargula, Renilla, Obelin, Porichthys, Odontosyllis, Aristostomias, Pachystomias*, firefly, and bacterial systems.

In another aspect the present invention relates to a system for generating electrical current, the system comprising:
- a) a substrate comprising mixed metal structures, wherein the metallic structures are at least partially covered with a polar solution;
- b) a set of electrodes communicatively contacting at least some of the mixed metal structures positioned thereon; and c) an intrinsic or extrinsic fluorophore positioned near the mixed metal structures, wherein when the fluorophore is excited by electromagnetic energy a mirror dipole is induced in the mixed metal structures causing plasmonic current flow for storage, directing to a current reading device or to provide sufficient amperage to power a device.

In another aspect, the present invention relates to a biosensing method for measuring concentration of an analyte that induces aggregation of mixed metal structures, the method comprising:
 a) preparing the mixed metal structures, wherein the mixed metal structures are coated with a binding component having an affinity for the analyte, and wherein the mixed metal structures are sized to scatters light according to the Rayleigh theory;
 b) exposing the mixed metal structures with electromagnetic radiation at a frequency that is at least scattered by the mixed metal structures;
 c) measuring the polarization of scattered light from the mixed metal structures;
 d) contacting the mixed metal structures with an analyte that has an affinity for the binding component; and
 e) measuring the polarization of scattered light emitted from the mixed metal structures, wherein the polarization decreases as aggregation increases.

In a still further aspect, the present invention relates to an assay using High Throughput Screening (HTS), the method comprising:
 a) providing a well plate used in HTS systems comprising a multiplicity of wells;
 b) introducing mixed metal structures into the wells, wherein the mixed metal structures are coupled to a binding receptor having affinity for a target molecule;
 c) introducing at solution suspected of including the target molecule for binding to the binding receptor;
 d) applying electromagnetic energy; and
 e) measuring the plasmonic emissions from the system during a predetermined time period. If polarization of the plasmonic emissions is being measured, the polarization values decrease as the binding of the target molecule increases.

For use in HTS plates, such as coated on 96-well and 384 well plates, the mixed metal structures increase the brightness of close proximity fluorophore and photostability as well as the dwell time for sampling the luminescence in a well.

Other aspects and advantages of the invention will be more fully apparent from the ensuing disclosure and appended claims.

DETAILED DESCRIPTION OF THE INVENTION

Figure 1:
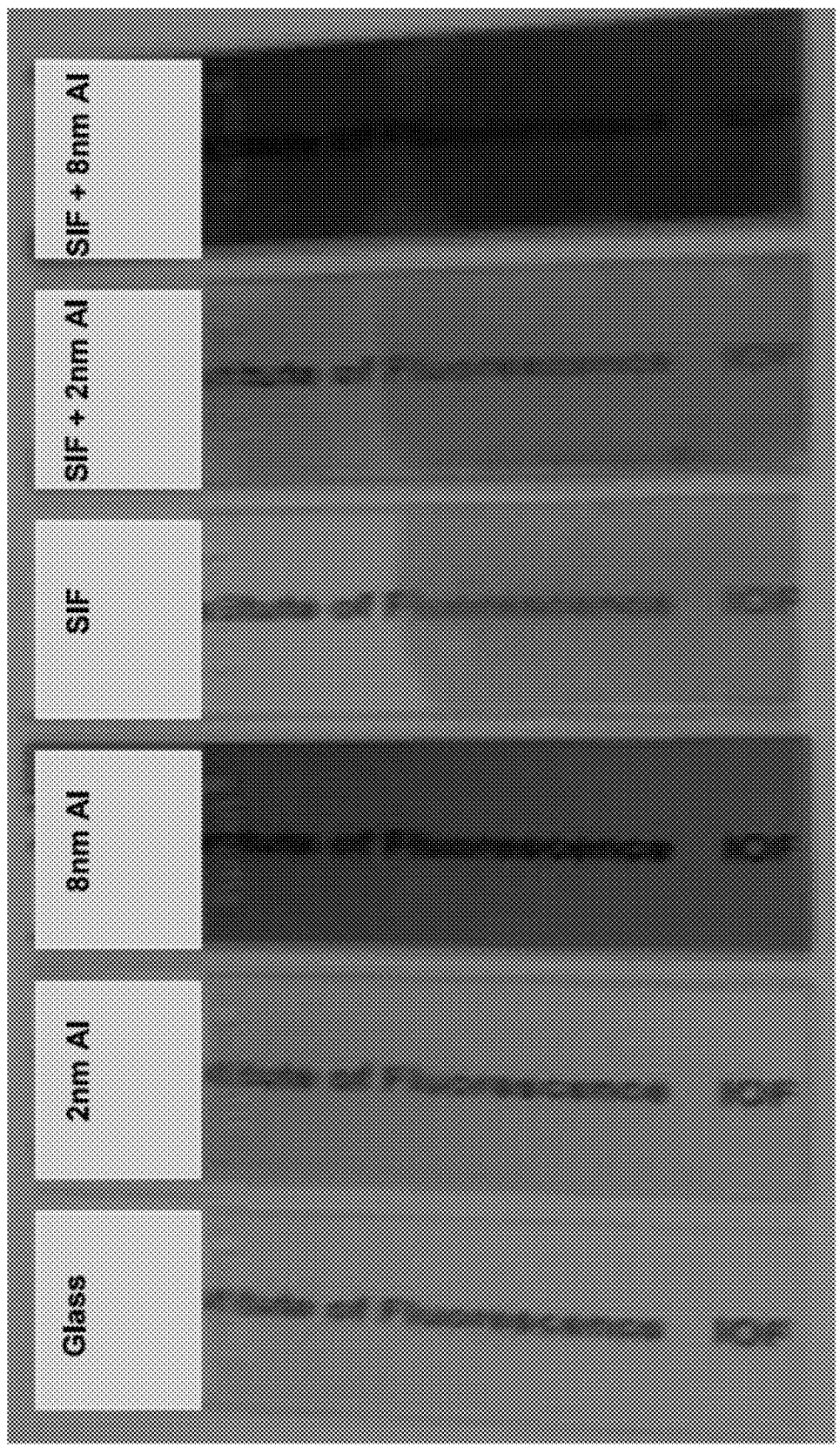
FIG. 1 shows photographs of the mixed metal substrates of the present invention.

Before the present invention is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural references unless the content clearly dictates otherwise.

The term "biomolecule" means any carbon based molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide nucleic acids, fatty acids, sugar groups such as glucose etc., vitamins, cofactors, purines, pyrimidines, formycin, lipids, phytochrome, phytofluor, peptides, lipids, antibodies and phycobiliproptein.

Fluorophore," and "fluorescence label," used interchangeably herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids including but not limited to 1-anilinonaphthalene-8-sulfonic acid (ANS) and 6-(p-toluidinyl) naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1, 4', 6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrirmidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Fluorophores with high radiative rates have high quantum yields and short lifetimes. Increasing the quantum yield requires decreasing the non-radiative rates $k_{nr}$, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_0$) and could significantly reduce unwanted background emission from fluorophores distal from the silvered assay.

Fluorophore photostability is a primary concern in many applications of fluorescence. This is particularly true in single molecule spectroscopy. A shorter lifetime also allows for a larger photon flux. The maximum number of photons that are emitted each second by a fluorophore is roughly limited by the lifetime of its excited state. For example, a 10 ns lifetime can yield about $10^8$ photons per second per molecule, but in practice, only $10^3$ photons can be readily observed. The small number of observed photons is typically due to both photo-destruction and isotropic emission. If a metal surface decreases the lifetime, one can obtain more photons per second per molecule by appropriately increasing the incident intensity.

On the other hand, the metal-enhanced fluorescence provides enhanced intensity, while simultaneously shortening the lifetime. That is, it may be possible to decrease the excitation intensity, yet still see a significant increase in the emission intensity and photostability.

The emission enhancement may be observed at distances according to the type of fluorophore to be detected and the type, shape of the metal material, noting a difference between a film and a metallic island or colloid. For example, emission enhancement may be observed when a fluorophore distances about 5 nm to about 200 nm to metal surfaces. Preferable distances are about 5 nm to about 30 nm, and more preferably, 5 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Attaching of the fluorophore to a probe may be achieved by any of the techniques familiar to those skilled in the art. For example, the fluorophore may be covalently attached to the bimolecular probe by methods disclosed in U.S. Pat. No. 5,194,300 (Cheung) and U.S. Pat. No. 4,774,189 (Schwartz).

In another embodiment, the assay system of the present invention provides for detecting and separating at least two target pathogen by choosing fluorophores such that they possess substantially different emission spectra, preferably having emission maxima separated by greater than 10 nm, more preferably having emission maxima separated by greater than 25 nm, even more preferably separated by greater than 50 nm. When differentiation between the two fluorophores is accomplished by visual inspection, the two dyes preferably have emission wavelengths of perceptibly different colors to enhance visual discrimination. When it is desirable to differentiate between the two fluorophores using instrumental methods, a variety of filters and diffraction gratings allow the respective emission maxima to be independently detected.

Any chemiluminescent species may be used in the present invention that provides for a chemical reaction which produces a detectable reaction (observed emission) wherein the excited state responsible for the observed emission including, but not limited to the following excitation mechanisms:

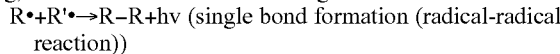
R•+R'•→R–R+hv (single bond formation (radical-radical reaction))

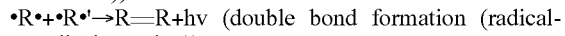
•R•+•R•'→R=R+hv (double bond formation (radical-radical reaction))

$RO_2•R•+O_2 \rightarrow R+hv$

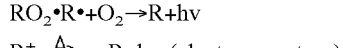
$R^+ + \text{e}^- \rightarrow R+hv$ (electron capture)

Examples of suitable chemiluminescence detector molecules include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, a Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen. Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio) proprionate (hereinafter SPDP) separately.

SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

The present invention provides enhanced emissions using metallic structures of elliptical, spherical, triangular, rod-like forms or any geometric form. In exemplary cases, the elliptical islands have aspect ratios of 3/2, and the spherical colloids have diameters of 20-60 nm. Using known coating techniques, the placement of metallic structures could be controlled precisely, as close as 50 nm apart.

Further, the metallic structures can be fabricated to form a geometric shape such as triangle, square, oblong, elliptical, rectangle, or any shape that provides at least one apex area of the metallic surface. It is envisioned that the apex area includes not only pointed regions but regions with rounded edges such as found in an oblong or elliptical shape. The apex areas are preferably arranged so that one apex area is opposite from another apex area and aligned to cause the reactive zone to be positioned therebetween. The distances between the apex areas may range from 0.01 mm to 5 mm, more preferably from 2 mm to about 3 mm and depending on the size of the required reactive zone. The thickness of the metallic geometric shaped forms ranges from 25 nm to about 1000 nm, and more preferably from about 45 nm to about 250 nm.

The present invention further comprises a detection device for detecting emissions including, but not limited to visual inspection, digital (CCD) cameras, video cameras, photographic film, or the use of current instrumentation such as laser scanning devices, fluorometers, luminometers, photodiodes, quantum counters, plate readers, epifluorescence microscopes, fluorescence correlation spectroscopy, scanning microscopes, confocal microscopes, capillary electrophoresis detectors, or other light detector capable of detecting the presence, location, intensity, excitation and emission spectra, fluorescence polarization, fluorescence lifetime, and other physical properties of the fluorescent signal.

Excitation light sources can include arc lamps and lasers, natural sunlight, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources. The enhanced sensitivity of the assay using 2-photon excitation, as compared to 1-photon, can be shown by using series dilution with RNA, initially with the Ti-Sapphire system, and later with LEDs and LDs. If a fluorophore absorbs two photons simultaneously, it will absorb enough energy to be raised to an excited state. The fluorophore will then emit a single photon with a wavelength that depends on the fluorophore used and typically in the visible spectra. The use of the Ti-sapphire laser with infrared light has an added benefit, that being, longer wavelengths are scattered less, which is beneficial for high-resolution imaging. Importantly, there is reduced background signal level gained by using 2-photon excitation as compared to 1-photon excitation by utilizing localized excitation near by metallic particles.

In one embodiment, the application of low level microwave heating of the sample may be used to speed up any chemical/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the metallic structures, which is contrary to most metal objects, such as that recognized by placing a spoon in a microwave oven.

Microwaves (about 0.3 to about 300 GHz) lie between the infrared and radiofrequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, where as microwaves are effectively transparent to hexane, toluene and diethylether. For metals, the attenuation of microwave radiation arises from the creation of currents resulting from charge carriers being displaced by the electric field. These conductance electrons are extremely mobile and unlike water molecules can be completely polarized in 10-18 s. In microwave cavity used in the present invention, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles. Interestingly, and most appropriate for the new assay platform described herein, small metal particles do not generate sufficiently large potential differences for this "arcing" phenomenon to occur. However, as discuss hereinbelow, the charge carriers which are displaced by the electric field are subject to resistance in the medium in which they travel due to collisions with the lattice phonons. This leads to Ohmic heating of the metallic structures in addition to the heating of any surface polar molecules. Intuitively, this leads to localized heating around the metallic structures in addition to the solvent, rapidly accelerating assay kinetics.

In the present invention, microwave radiation may be provided by an electromagnetic source having a frequency in a range between 0.3 and 10 GHz and a power level in a range between about 10 mwatts and 400 watts, more preferably from 30 mwatts to about 200 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy and energy to excite fluorescing molecules. The light can be emitted from a fiber continuously or intermittently, as desired, to maintain the metallic particles at a predetermined temperature such that it is capable of increasing the speed of chemical reactions within the assay system. The microwave radiation may be emitted continuously or intermittently (pulsed), as desired.

In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

Although fluorescence, chemiluminescence and/or bioluminescence detection has been successfully implemented, the sensitivity and specificity of these reactions require further improvements to facilitate early diagnosis of the prevalence of disease. In addition, most protein detection methodologies, most notably western blotting, are still not reliable methods for accurate quantification of low protein concentrations without investing in high-sensitivity detection schemes. Protein detection methodologies are also limited by antigen-antibody recognition steps that are generally kinetically very slow and require long incubation times; e.g., western blots require processing times in excess of 4 h. Thus, both the rapidity and sensitivity of small-molecule assays are still critical issues to be addressed to improve assay detection. As such the use of low intensity ultrasound will increase the rapidity of the assay.

There are many important assays that can directly benefit from enhanced signal intensities and quicker kinetics. For example, myoglobin concentrations for heart attack patients, patients of toxic shock and pancreatitus. All of these assays are widely used in hospitals emergency rooms with assay times of greater than 30 minutes. Thus, the present invention can be used for points-of-care clinical assessment in emergency rooms.

Thus it would be advantageous to increase speed of any chemical or biochemical reaction by using any device capable of generating and transmitting acoustic energy through any medium to transit ultrasonic atomizing energy. The ultrasonic emitting device can be placed in either the interior of a vessel used in a detection system or positioned adjacent thereto for transmitting energy into the vessel. The device may include components for the traditional electromagnetic stimulation of piezoelectric transducers, (man-made or naturally occurring), purely mechanical devices (such as high frequency air whistles or microphones), and laser devices. Individual components for acoustic energy systems are commercially available from a wide variety of manufacturers, which can be configured to particular applications and frequency ranges. (See Thomas Directory of American Manufacturers, Photonics Buyer's Guide, 1996, Microwave and RF, and Electronic Engineer's Master Catalogue).

Any oscillator or signal generator that produces a signal with predetermined characteristics such as frequency, mode, pulse duration, shape, and repetition rate may be used to generate acoustic frequencies for applying to the system of the present invention. Various oscillators or signal generators can be commercially purchased from a wide variety of manufacturers and in a variety of designs configured to particular applications and frequencies. Applicable transducers will include types that produce an acoustic wave within a range of frequencies (broadband) or for one specific frequency (narrowband) for frequencies ranging from hertz to gigahertz.

The acoustic delivery system will be variable depending on the application. For example, acoustic energy waves can be transmitted into liquid or solid source material either by direct contact of the source material with a transducer, or by coupling of transmission of the acoustic wave through another medium, which is itself in direct contact with the source material. If the source material is a liquid, a transducer can be placed in the liquid source material, or the walls of the vaporization vessel can be fabricated of a material that acts as a transducer thereby placing the liquid source material in direct contact with the transducer. Additionally, an acoustic energy emitting device may be positioned on the exterior of a system container for transmitting the appropriate energy. If the source material is a solid, a transducer can be placed in direct contact with it or the solid source material can be placed in a gas or liquid that is used as a coupling agent.

In the preferred acoustic frequencies any system that generates acoustic energy may be utilized. Preferably, the output of the ultrasonic generator is of a sufficient frequency to provide a movement flow within the system vessel to move molecules to the source of binding or reaction site without causing a large increase of heat in the system. For example, using the power output of 0.5 to 50 W at a frequency of 10 to 200 kHz, and more preferably from about 20 to 60 kHz and most preferably at about 40 kHz.

To obtain the maximum transfer of acoustical energy from one medium to another, the characteristic acoustical impedance of each medium is preferably as nearly equal to the other as possible. The matching medium is sandwiched between the other two and should be the appropriate thickness relative to the wavelength of the sound transmitted, and its acoustical impedance R should be nearly equal to ($R_1$:$R_2$). Any impedance matching device that is commercially available can be utilized in the present invention.

The system may include ultrasonic vessels wherein at least a section of the vessel includes a transducer such as a piezoelectric transducer to generate acoustic vibrations. Such transducers can be located in the bottom of a vessel or in a plate whereon a vessel may be placed. Further such transducers can be placed at different levels on the vessel walls to enhance fluid flow within the vessel.

EXAMPLES

Materials and Methods

Materials. Toluene, Fluorescein, Rose Bengal, N-acetyl-tryptophan-amid (NATA) and Phenylalanine (Phe), were purchased from Sigma. The concentration of NATA and Phe were determined by measuring the optical density of the solutions using extinction coefficients of $E_{280}$=5,300 $M^{-1}$ $cm^{-1}$ and $E_{257}$=195 $M^{-1}$ $cm^{-1}$, respectively (26; 27). Bovine serum albumin (BSA) was purchased from Sigma. To determine the concentration of the protein in solutions, an extinction coefficient of $E_{280}$=43,824 $M^{-1}$ $cm^{-1}$ was used. Aluminum wire, 99% pure, for thermal vapor deposition onto glass slides was purchased from the Kurt J. Lesker Company, Material Group (Clairton, Pa.). Chromophores, including amino acids and protein, BSA, were dissolved in TE buffer, pH 7.4.

Measurements of absorption and fluorescence. Absorption spectra of the fluorophores, protein intrinsic chromophores and BSA were measured using a Varian Spectrophotometer in quartz B7 1-cm path-length cuvettes. Fluorescence spectra of the fluorophores and BSA were recorded using a Cary Eclipse spectrofluorimeter (Varian, Inc., USA) at room temperature. The solutions were sandwiched between a quartz slide and a glass slide with deposited metal(s) (silver, aluminum and their mixture) and for the control sample, containing no metal, between quartz/glass slides.

Time-resolved fluorescence decay measurements. The fluorescence intensity decay functions of the Fluorescein chromophore on metal slides of different composition and thickness, and on glass (MEF control sample) were measured using a TemPro Fluorescence Lifetime System (Horiba Jobin Yvon, USA). The reference cell contained colloidal silica, SM-30 ludox solution, used as a control (zero lifetime). Measurements were performed at room temperature. Determination of Fluorescein excited state lifetimes ($\tau_i$) and corresponding amplitudes ($\alpha_i$) were undertaken using the TemPro Fluorescence Lifetime System software, DAS 6.

The emission intensity decays were analyzed in terms of the multiexponential model:

$$[t] = \sum_i \alpha_i \exp[-t/\tau_i] \quad (1)$$

Where $\alpha_i$ are the amplitudes, the sum of which equals to 1.0, and $\tau_i$ are the decay times. The fractional contribution of each component to the steady-state intensity can be given as:

$$f_i = \frac{\alpha_i \tau_i}{\sum_j \alpha_j \tau_j} \quad (2)$$

The mean lifetime of the chromophore excited state was calculated using the following equation:

$$\bar{\tau} = \sum_i f_i \tau_i \quad (3)$$

The amplitude weighted fluorescence lifetime was calculated as follows:

$$\langle \tau \rangle = \sum_{i=1}^n \alpha_i \times \tau_i \quad (4)$$

where n is a number of fluorescence decay components in the total decay function. The values of the amplitudes and decay times were determined using nonlinear least-squares impulse reconvolution with a goodness-of-fit $\chi^2$ criterion.

Numerical FDTD simulations. The 2D computational simulations of the electric field intensities and near-field distributions around metal nanoparticles were undertaken for three systems: a) two 250 nm silver nanoparticles separated by 40 nm free space; b) 30 nm aluminum nanoparticle (NP) and c) their mixture—30 nm aluminum NP is centered between two 250 nm silver NPs, separated by 40 nm, using the Finite Difference Time Domain (FDTD) method. TFSF (total field scattered field) sources are used to divide the computation area or volume into total field (incident plus scattered field) and scattered field only regions. The incident p-polarized electric field was defined as a plane wave with a wave-vector that is normal to the injection surface. Using FDTD Solution software (Lumerical, Inc. http://www.lumerical.com), the simulation region was set to 700×450 nm² with a mesh accuracy of 5. To minimize simulation times and maximize resolution of field enhancement regions around the particle arrangement, a mesh override region is set to 1 nm around the nanoparticles. The overall simulation time was set to 50 fs and calculated over a broad wavelength range, using known permittivity values and refractive indices of silver and aluminum. The wavelength dependence of the NPs extinction, and cross-sections of its components, absorption and scattering, were calculated using Lumerical software script. To simulate effects of water polarity on plasmon resonance spectra, the background index was set to the corresponding refractive index of water, 1.333.

Preparation of Silver-island Films (SiFs). Silver-island films were prepared according to the procedure found in reference (3). Deviations in SiF thickness were reduced by using a fresh selection of Silane-Prep™ slides. The slides were stored in a vacuum between SiFs preparations to reduce possible oxidation.

Thermal vapor deposition of Aluminum onto glass slides and on silver coated slides (SiFs) was performed using an AUTO 306 Vacuum Coater instrument, equipped with SQM-160 Rate/Thickness Monitor (BOC Edwards, USA). Thickness of the deposited aluminum on glass slides and on slides coated with silver nanoparticles (SiFs) ranged from 2 to 16 nm, as measured using the quartz-crystal microbalance. Real-color photographs of the aluminum and mixed (aluminum+silver) slides, used in this study, are shown in FIG. 1.

Figure 2:
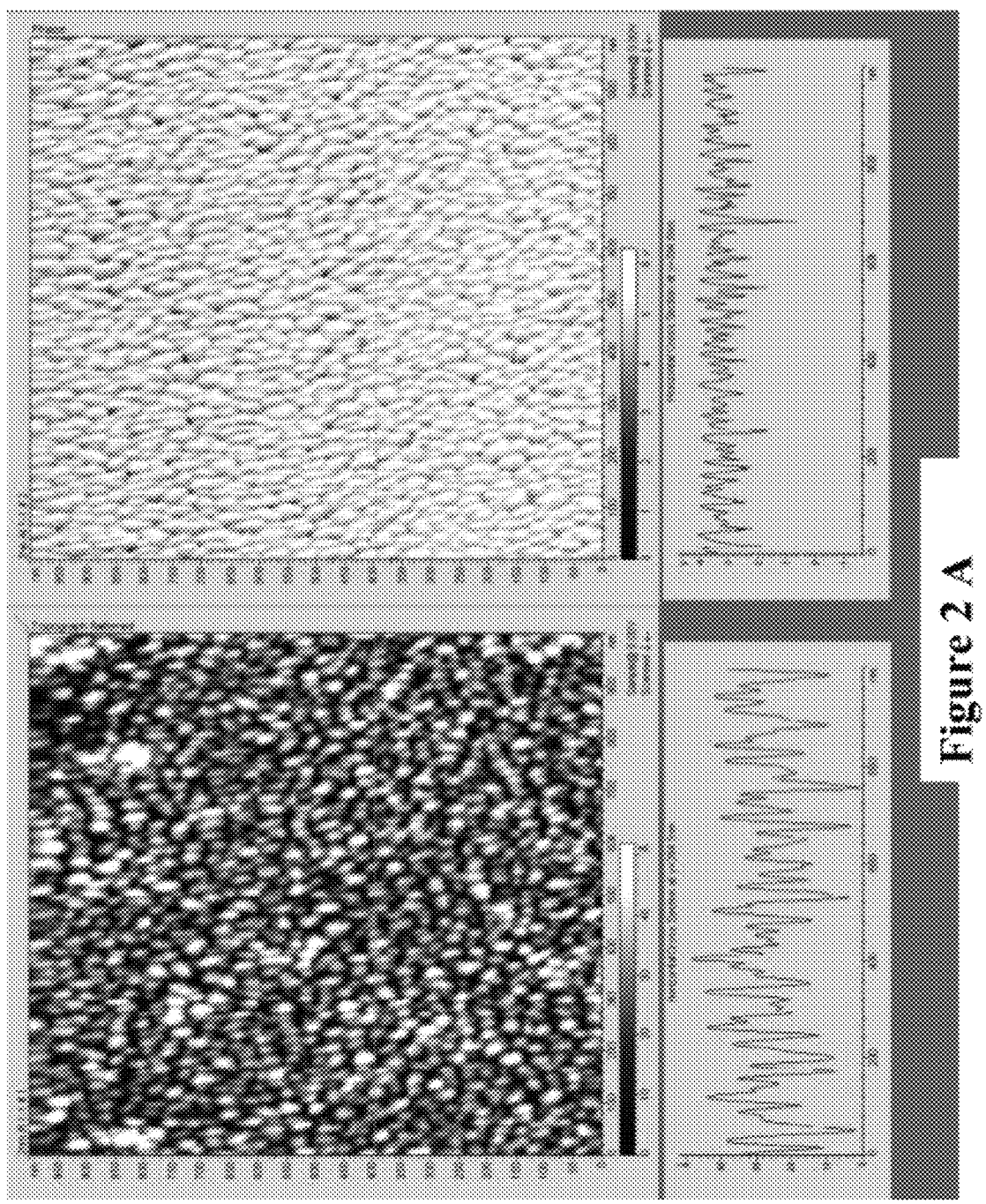
FIG. 2 shows AFM and phase images of Aluminum substrates. a) AFM images of 2 nm Al on glass (Left). Phase images (Right). Below are the respective line scans for the AFM images. (b) AFM images of 6 nm Al on glass (Left). Phase image (Right). Below are the respective line scans for the AFM images.
Figure 2B:
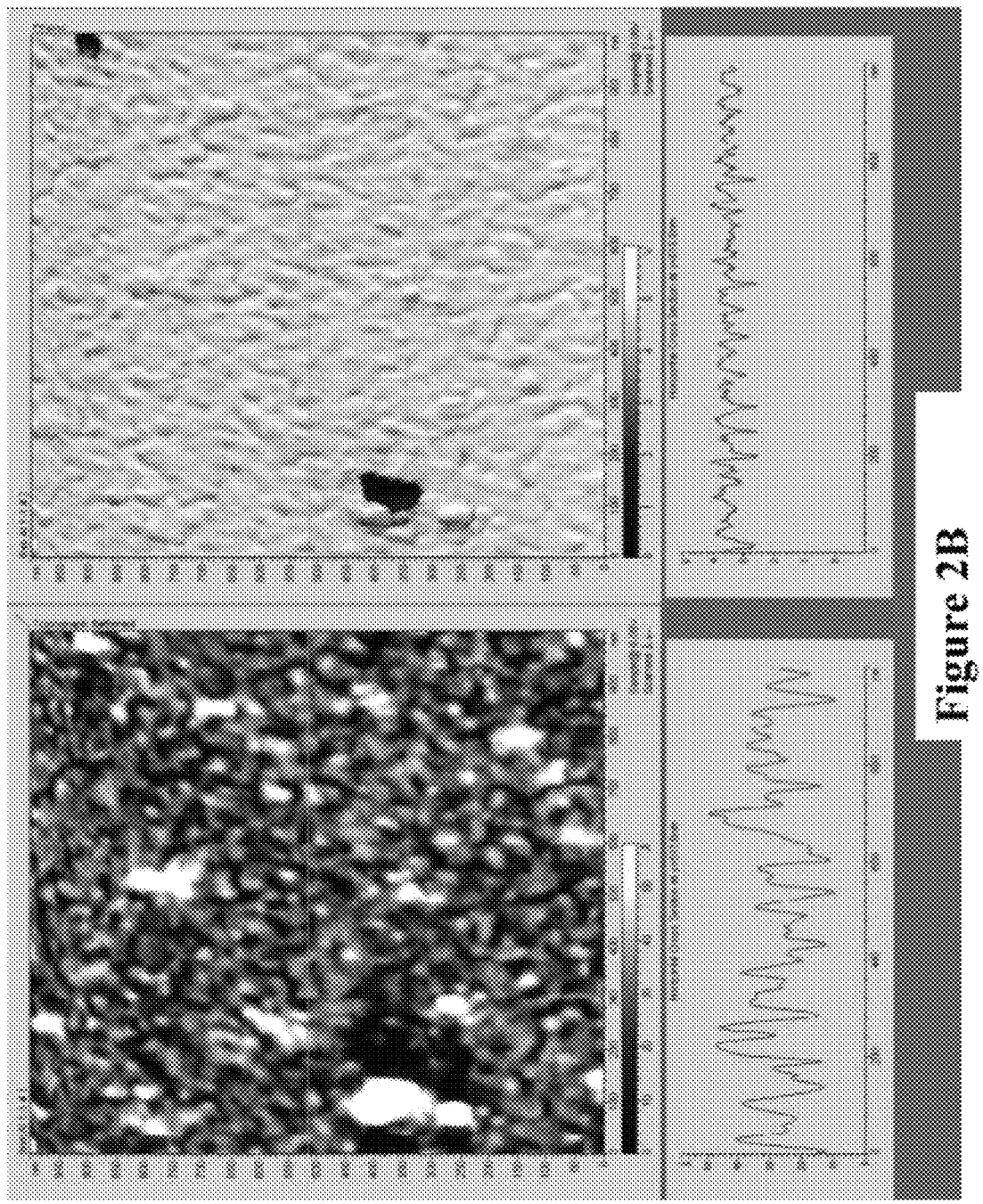
Figure 3A:
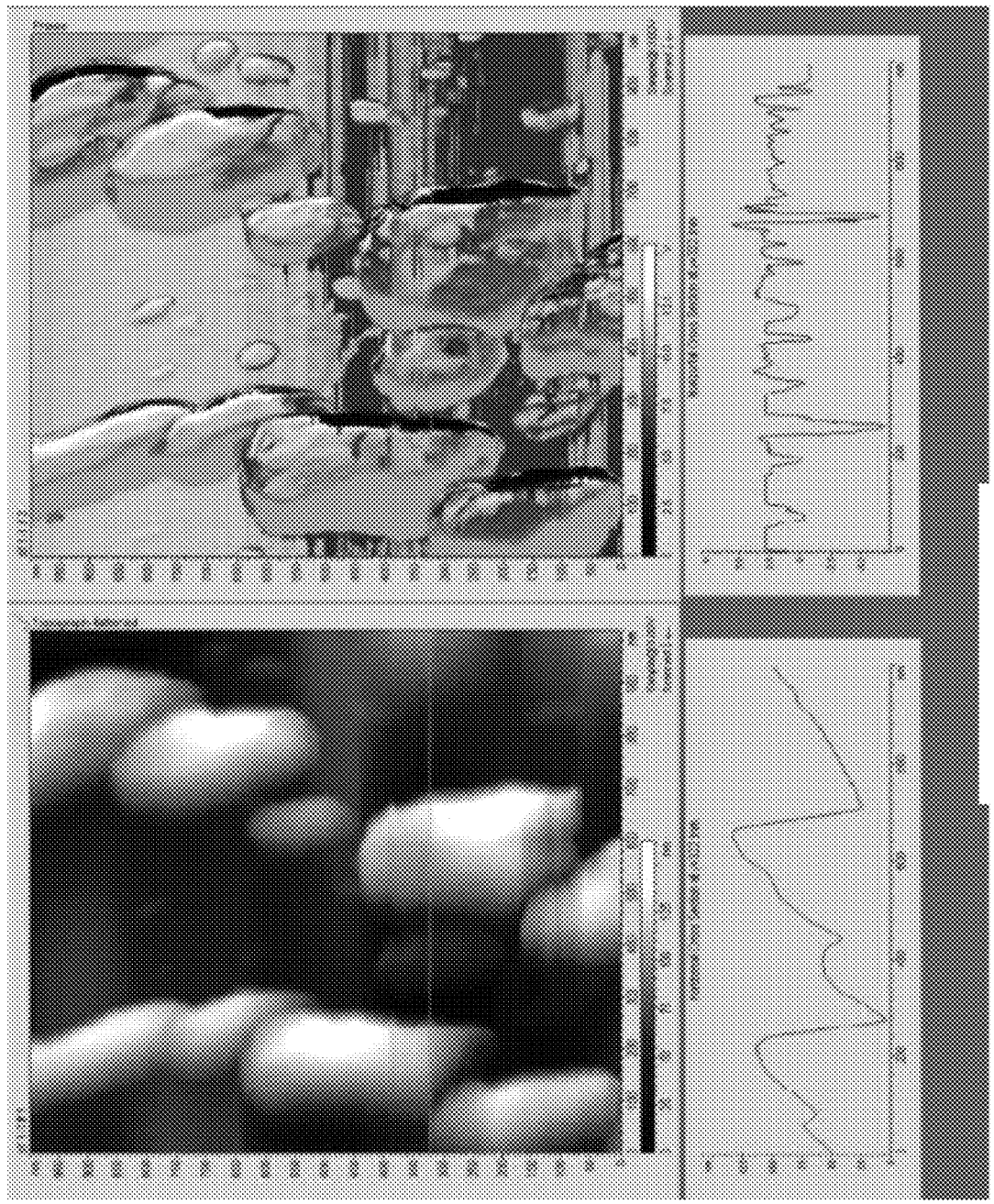
FIG. 3 shows AFM and phase images of Aluminum coated SiFs substrates. (a) AFM images of SiFs (Left). Phase image (Right). Below are the respective line scans for the responding AFM images. (b) AFM images of 2 nm Al on SiFs (Left), phase image (Right). Below are the respective line scans for the AFM images.
Figure 15:
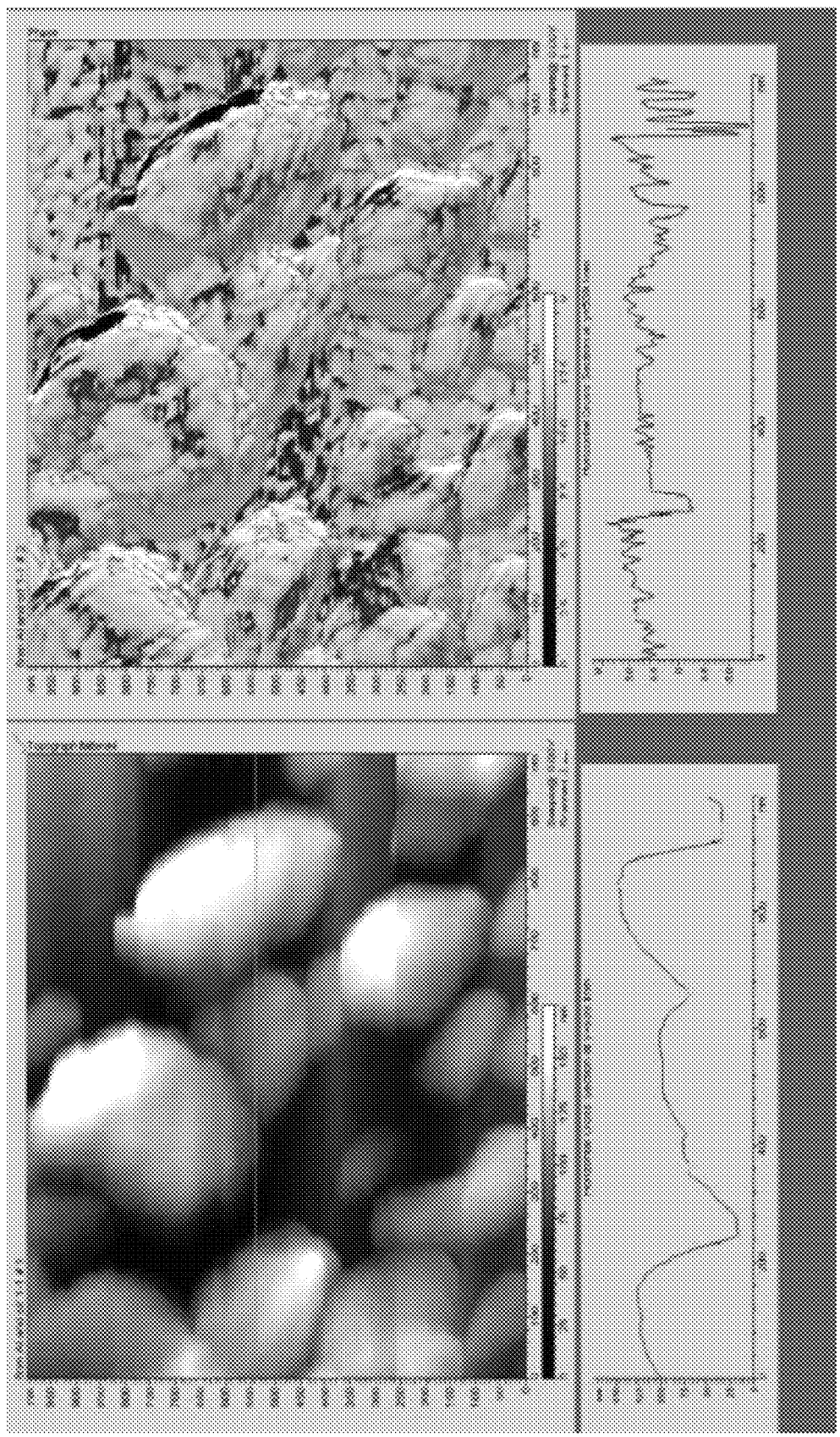
FIG. 15 shows AFM images of 8 nm Al on SiFs (Left). Phase image (Right). Below are the respective line scans for the AFM images.
Figure 16:
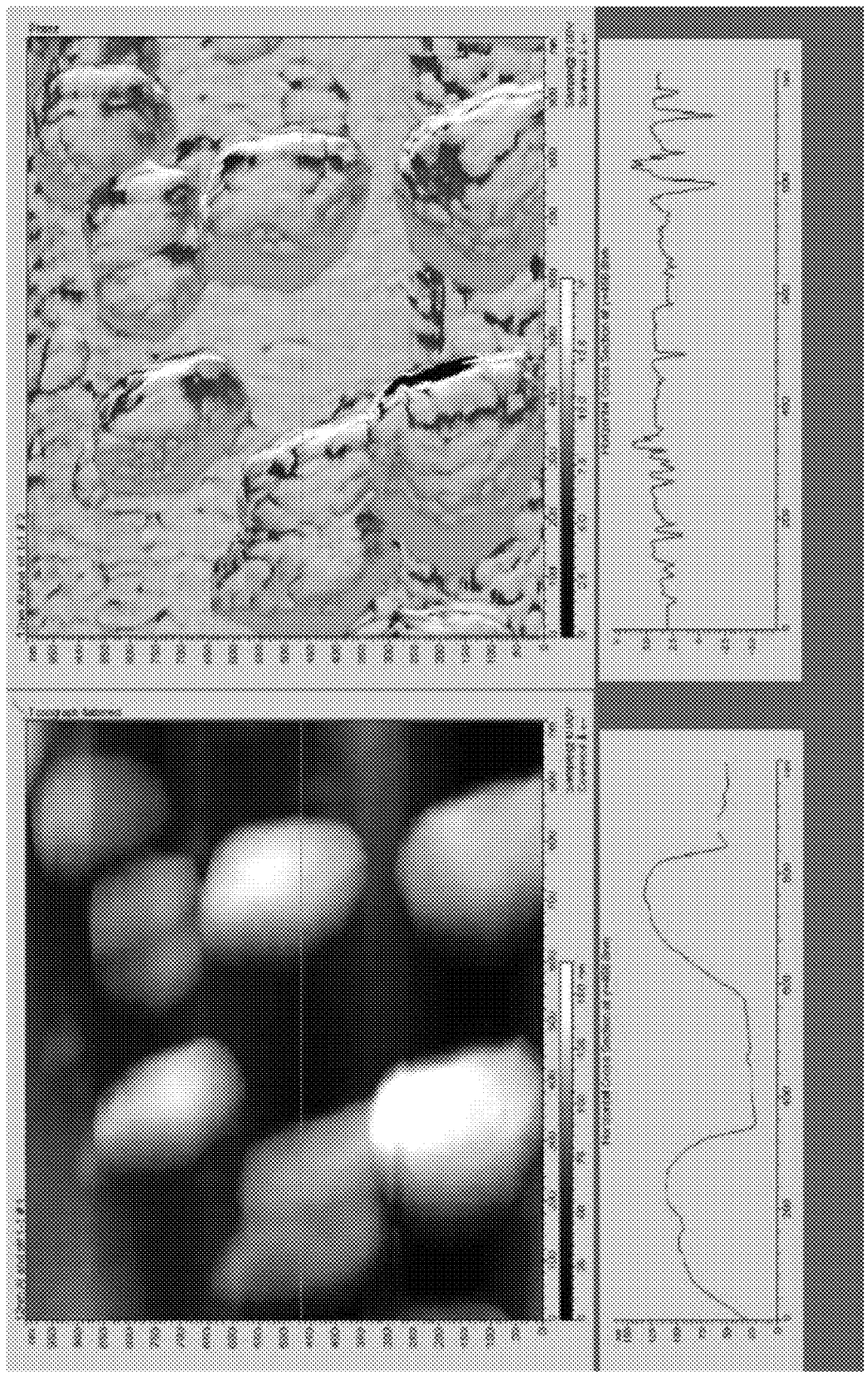
FIG. 16 shows AFM images of 12 nm Al on SiFs (Left). Phase image (Right) Below are the respective line scans for the AFM images.
Figure 17:
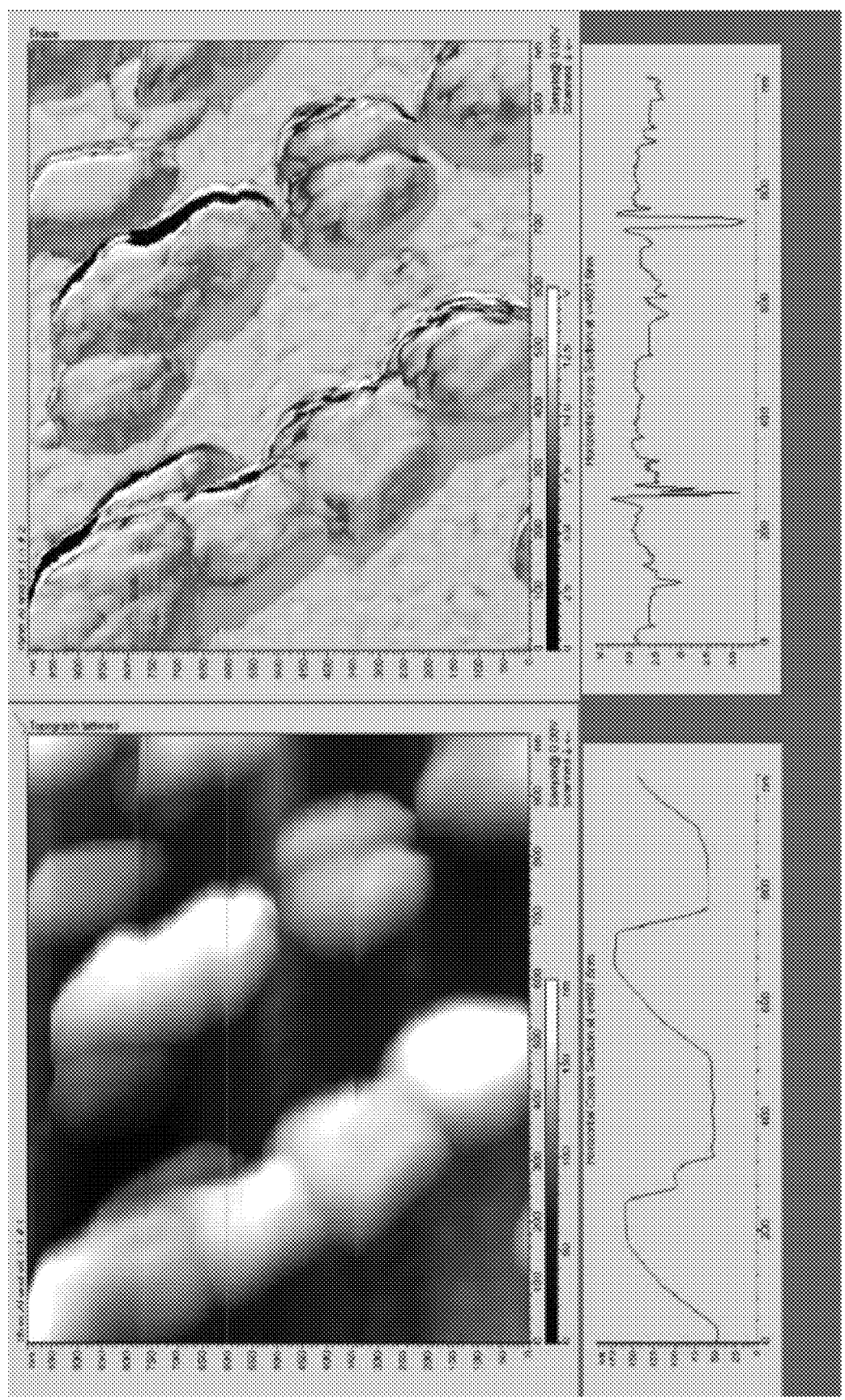
FIG. 17 shows AFM images of 16 nm Al on SiFs (Left). Phase image (Right). Below are the respective line scans for the AFM images.

To study the effects of mixed-metal substrates (MMS) on enhanced fluorescence intensities, Aluminum was thermally evaporated onto glass substrates containing preformed silver-island films (SiFs), where individual both SiFs and Aluminum slides also served as control samples. As a function of Aluminum deposition, the slides are seen to become increasingly optically dense as evidenced by the photographs within FIG. 1, left to right. AFM images for 2 nm Aluminum deposits on glass, FIG. 2a, show surfaces comprised of small "rice like" nanoparticles, more evident in the phase contrast image of FIG. 2a right. As the thickness of the Aluminum is increased, FIG. 2b, the surface appears much more continuous. In contrast, AFM images of SiFs deposits on glass show much bigger island deposits, consistent with recent reports, FIG. 3a (28). However, when 2 nm Aluminum is deposited on the SiFs, we see the "rice like" structures effectively coating the SiFs, FIG. 3b, the phase contrast images, right, showing the Aluminum nanostructured texture over the SiFs. The horizontal line scan of FIG. 3b also shows an increase in surface roughness between the SiFs and coated SiFs samples, c.f., FIG. 3a right and 3b right images. Similarly, FIGS. 15 to 17, show Aluminum deposits on SiFs for 8, 12 and 16 nm of Aluminum respectively.

Figure 4:
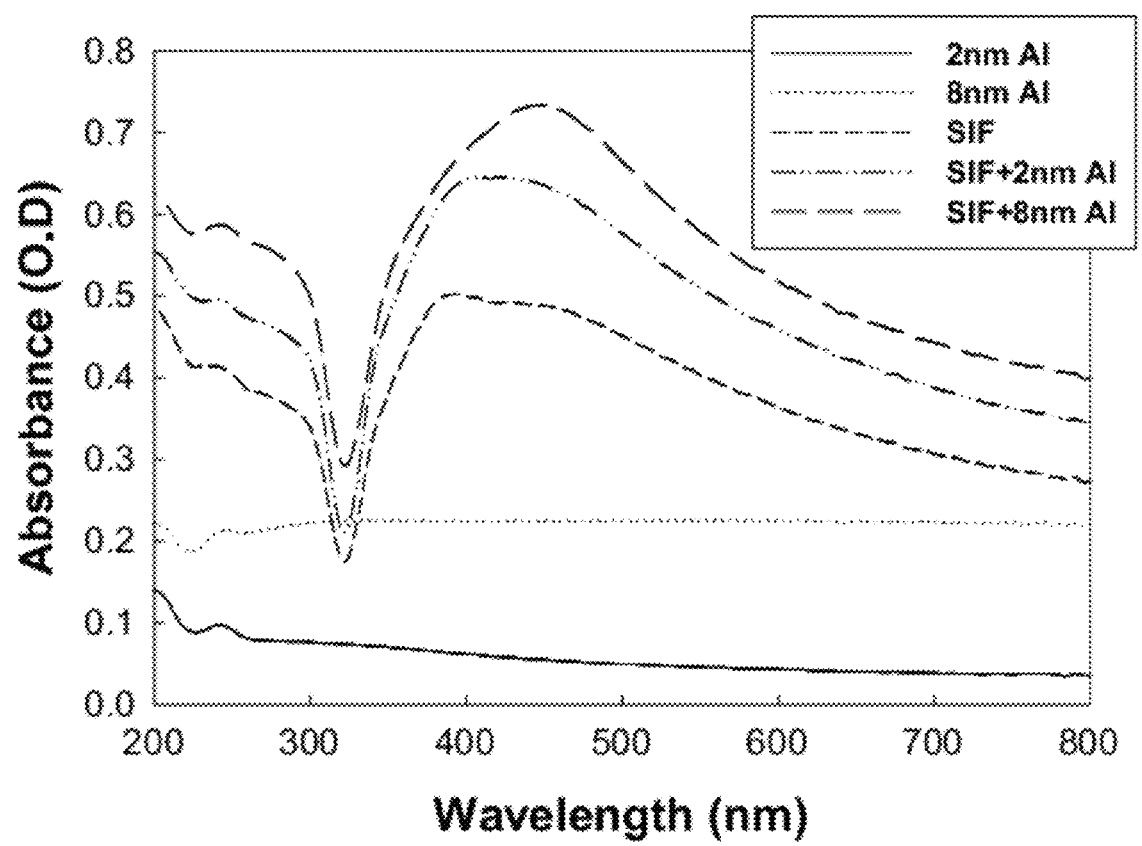
FIG. 4 shows the optical absorption spectra of the mixed metal substrates of the different metalized slides as shown in FIG. 1. Interestingly, the plasmon absorption spectra shifts as more and different metal is applied/deposited to the surface.

Absorption spectra of the samples, FIG. 4, shows that both 2 and 8 nm Aluminum coatings appear optically mirror like, with a somewhat flat absorbance until the deep UV, where the band at 250 nm is indicative of the Plasmon absorbance of Aluminum. The SiFs absorption spectra shows the typical strong plasmon resonance bands from 380 to 500 nm (28), which both broadens and increases in optical density for the thicker coatings of Aluminum on the SiFs. This is consistent with the color photographs in FIG. 1, which also become less transparent for thicker Aluminum coatings.

Figure 3:
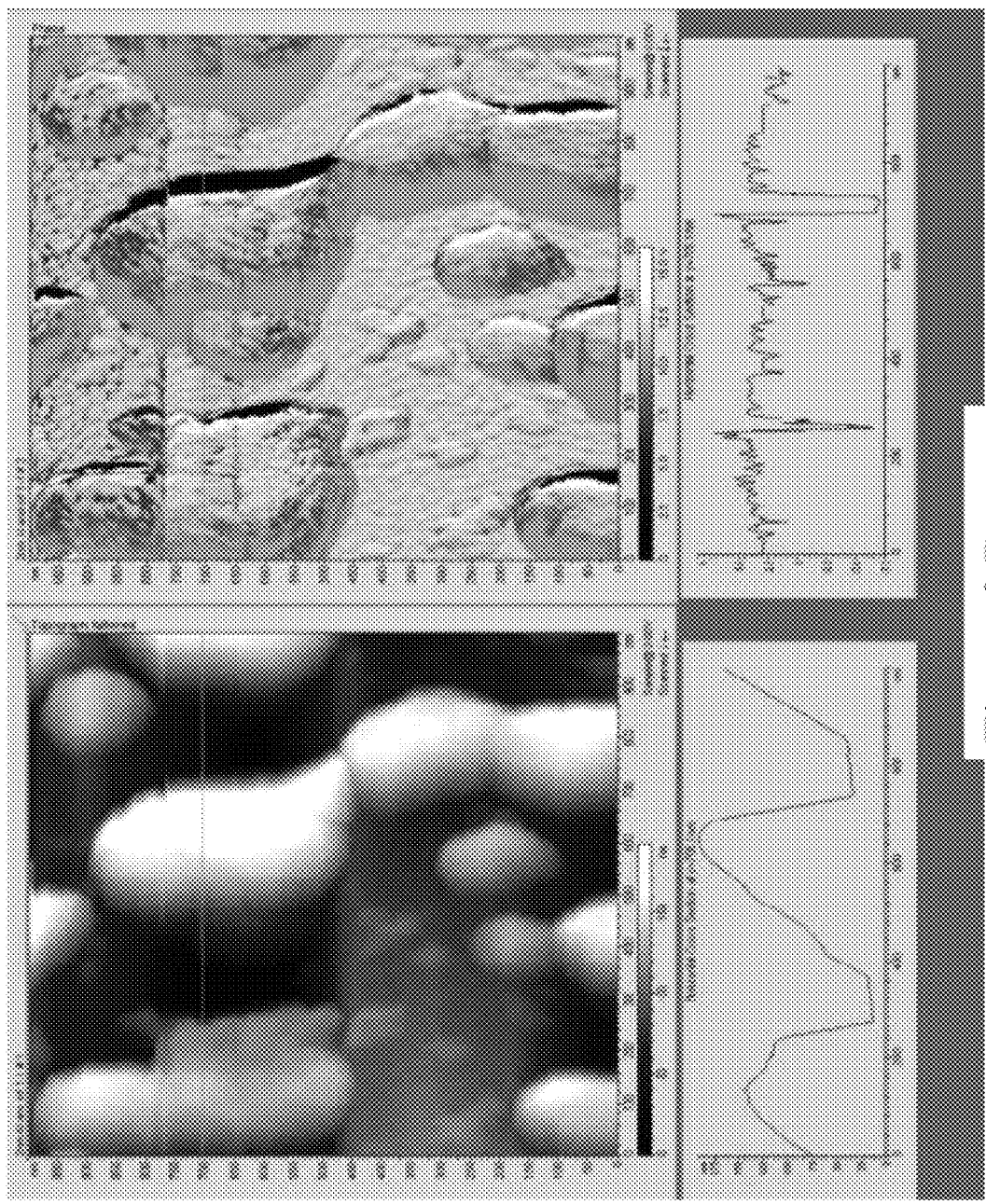
Figure 5:
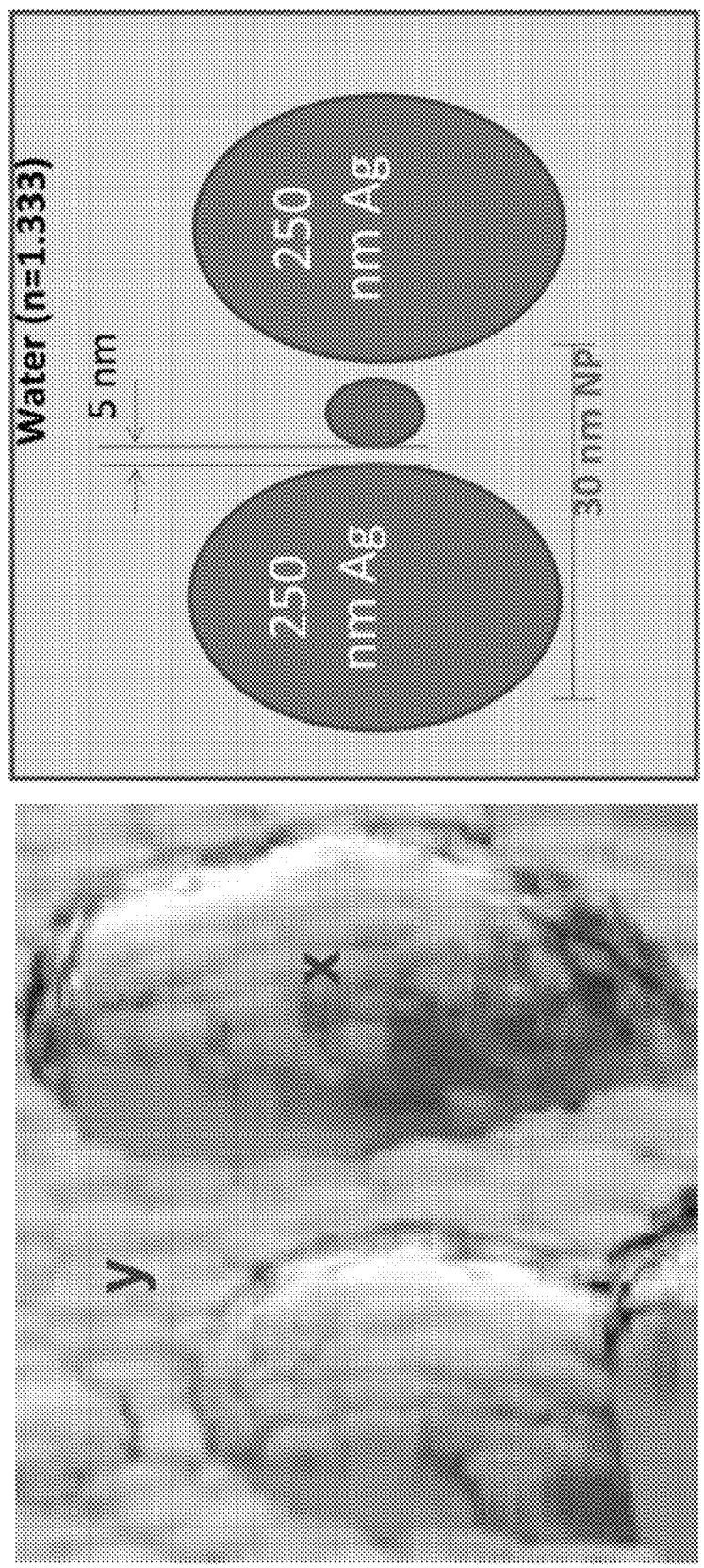
FIG. 5 shows AFM images of two silver-NPs and aluminum NPs deposited on the SiF surface. Left is an enhanced region from FIG. 3 for which the theoretical numerical simulations were modeled upon. Right shows the details of the simulations, approximated from the left hand side image. The simulations were undertaken to understand why the enhancement factors were higher for the mixed metals as compared to the single metals alone.

To understand these colorimetric and optical density changes, Finite Difference Time Domain (FDTD) Simulations was undertaken, in essence numerical simulations to both explain and account for the experimental observations. FIG. 5 shows a region-of-interest (ROI) which has been selected from the AFM images of FIG. 3. Interestingly, the enlarged ROI clearly shows the Aluminum "rice like" deposits (Region Y) on the SiFs (Region X).

Figure 6:
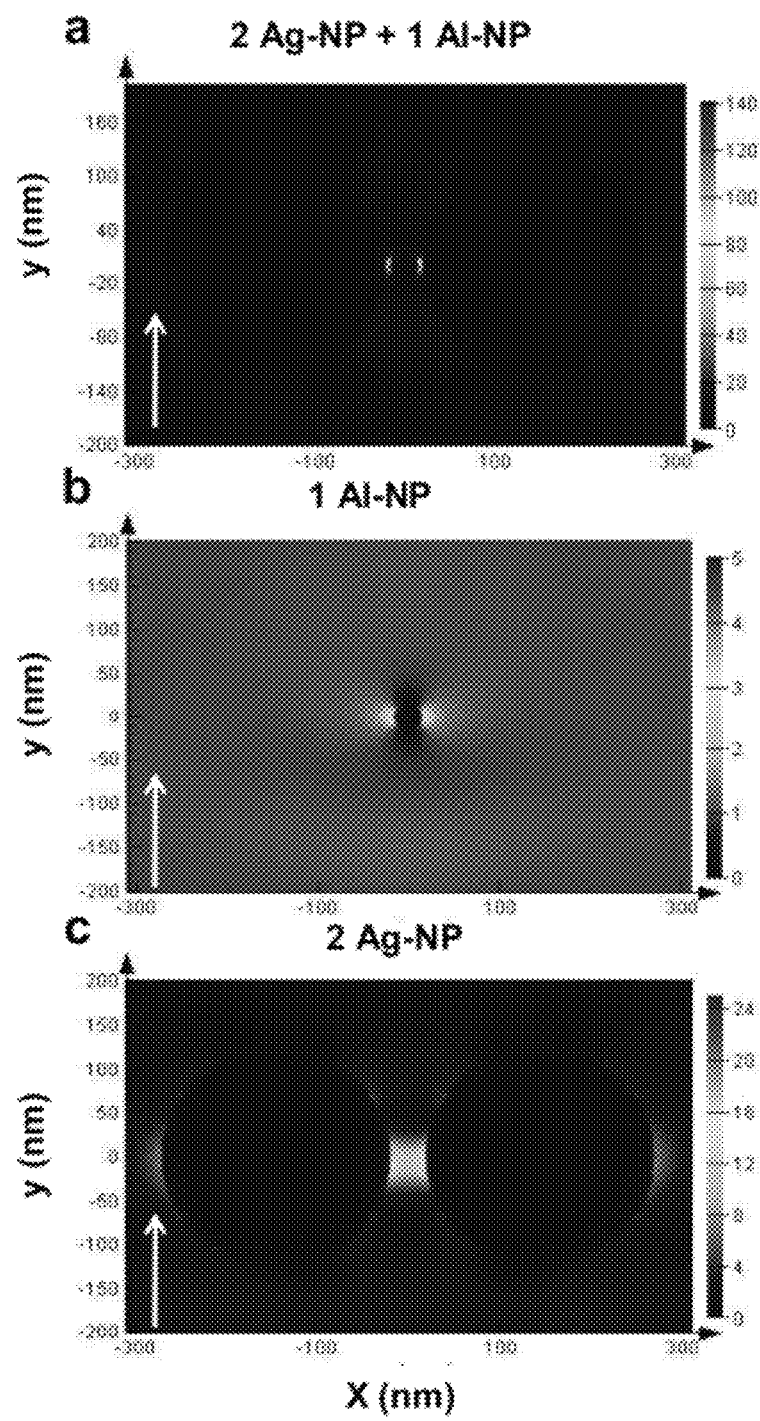
FIG. 6 shows the FDTD (finite difference time domain) simulations for aluminum nanoparticles between 2 silver islands. This configuration is similar to what is observed in the AFM images of FIG. 5 left. The simulations reveal that the electric field is much higher between the silver colloids when the aluminum nanoparticles are present. Arrows denote the injection axis in the FDTD simulations.
Figure 18:
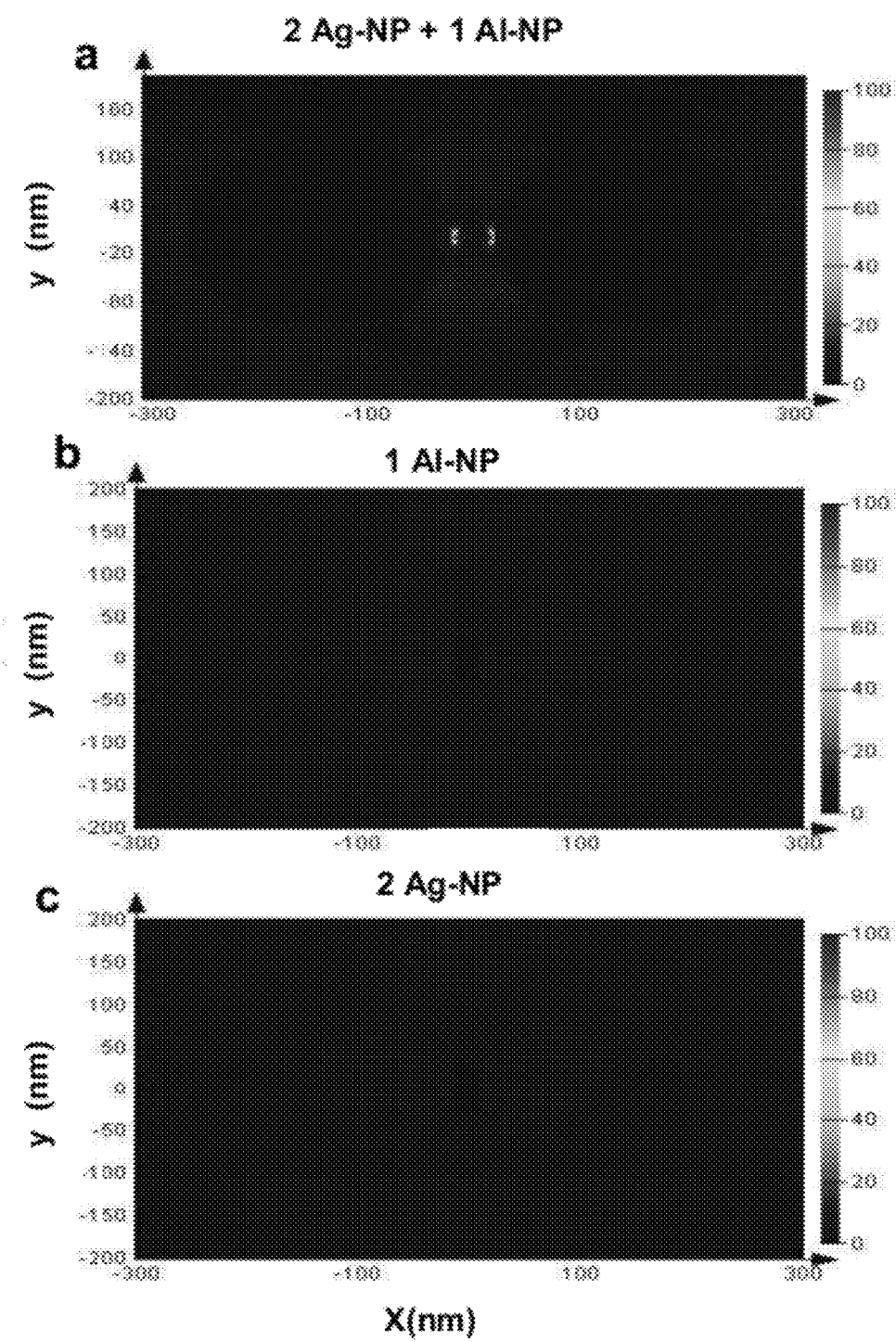
FIG. 18 shows E-field around Al- and Ag-NPs normalized to the same near field $|E|^2$ intensity. Insertion of 30 nm Al NP between 250 nm Ag NPs enhances E-field 4-5-fold not only between NPs but also surrounding the particles and builds on our simulation work and shows the benefit of mixed metals on the e-field intensity, which is clearly visible for the mixed metal case (a), but is not visible for the single metal particles when the field is normalized to 100, panels (b) and (c).

FIG. 6 shows the respective Theoretical Electrical Field simulations for the model. For the case of just two silver nanoparticles, FIG. 6c, a modest E-field intensity is seen between the nanoparticles, considerably greater in magnitude than for the single Aluminum particle shown in FIG. 6b. FIG. 6a shows the significantly enhanced electric field for the case of two Silver nanoparticles and one centered Aluminum nanoparticle. It is important to note the Y-axis intensity scales for each respective image. The significant increases in electric field strength are further visualized when considering the respective normalized plot of FIG. 6 and FIG. 18. In these figures, one only sees an electric field in the top portion of the images, i.e. for the two silver and one aluminum nanoparticle constructs.

It has been previously postulated that the mechanism underpinning MEF to be comprised of both an enhanced absorption (i.e. enhanced electric field effect) as well as an enhanced plasmon coupling component, the extent of MEF luminescence enhancement underpinned by the spectral overlap of a fluorophores' emission spectra with the plasmon-scattering component of a nanoparticles' extinction spectra (16). This second mode of fluorescence enhancement has recently been experimentally verified, (16), and manifests itself by a shorter system luminescence/fluorescence lifetime, the surface plasmons in essence radiating the coupled quanta, in a system which is coupled in both the ground and excited state (16).

Figure 7A:
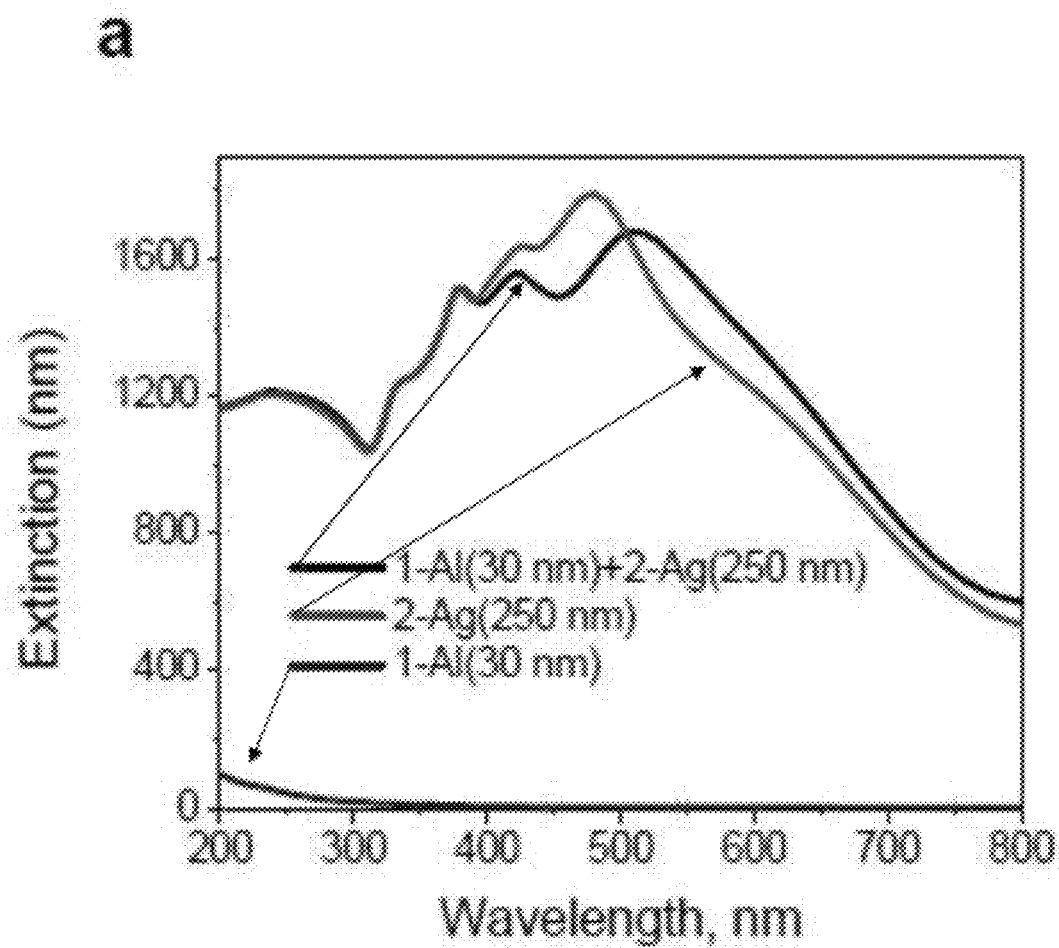
FIG. 7 shows the calculated extinction, absorption and scattering spectra for the NPs in water. The spectra were calculated using the model/geometry shown in FIG. 5 right. (a) Extinction; (b) absorption; (c) scattering spectra of NPs in water.

Subsequently to further understand the plasmon-coupling component in MEF mixed metal substrates, further simulations have been undertaken FIG. 7. FIG. 7 shows the extinction spectra (a), absorption (b) and scattering components (c) for the 3-particle model. Interestingly, all three spectra are typically broader for the 2 Ag and 1 Al nanoparticle system i.e. that considered in our ROI, FIG. 5. Surprisingly, deconvolution of the respective spectra shows the presence of a new plasmon resonance band at ≈540 nm, not present in the plasmon absorption spectra of the two individual metals themselves, FIG. 8. At this time it is believed that the new resonance band is due to the coupling and high-frequency dephased resonance of the surface plasmons from both metal types, not unlike the dephasing of similar resonances for identical metals, which have been shown to couple up to 2.5 times their diameter (6). Interestingly, the ROI AFM image of FIG. 5, clearly shows the same particles are within this geometrical coupling consideration. It is worth noting that this model considers particles which are spatially separated and no model has been considered for the case of the Al directly coated onto the SiFs, which is far more complex, both sample embodiments present in FIG. 5.

Figure 9:
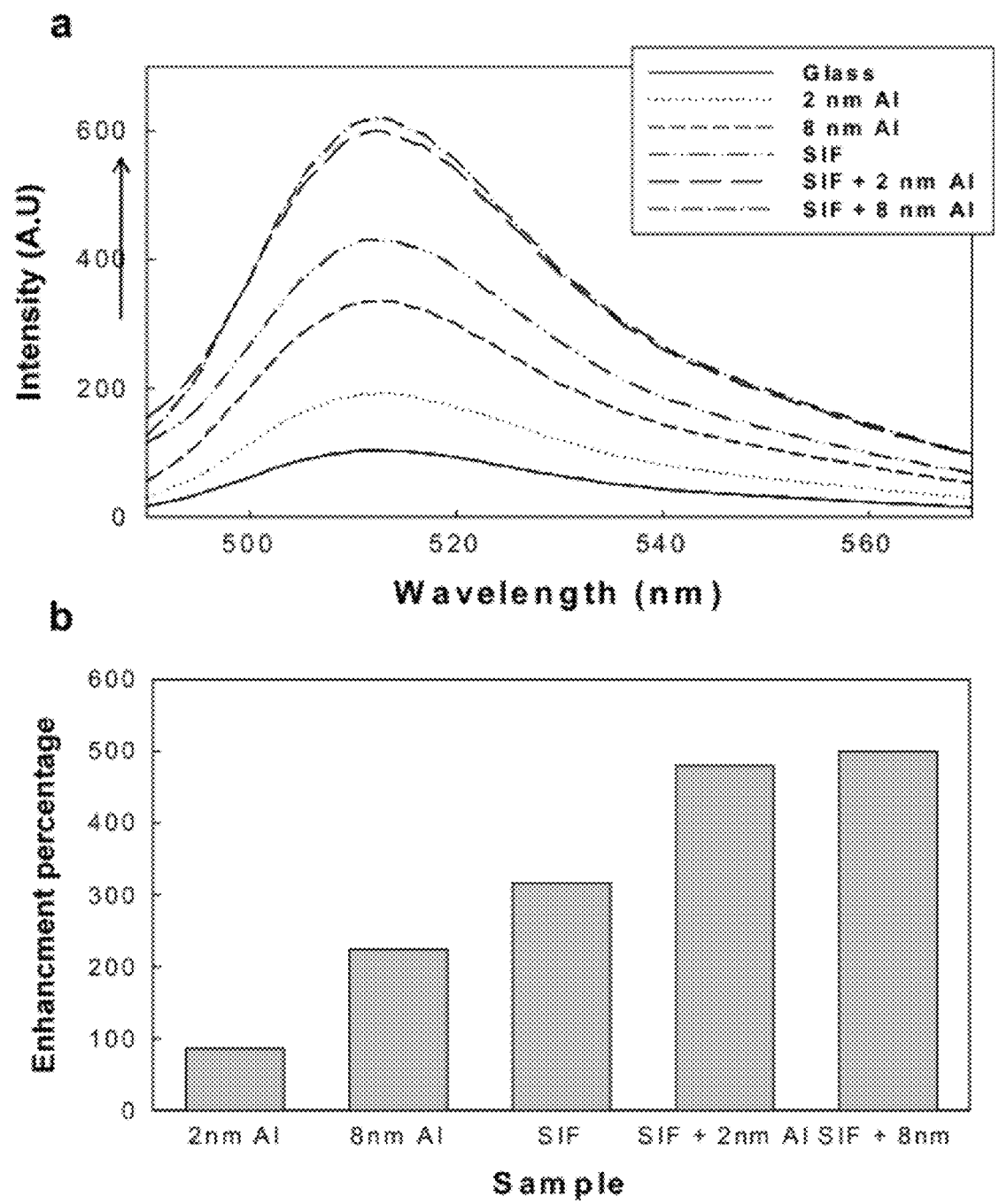
FIG. 9 shows the enhanced fluorescence from a fluorescein solution excited above the different metalized substrates. Interestingly, a 500% increase in signal is observed for Al coated SiFs, suggesting that mixed metal substrates have utility for enhancing fluorescence signatures. Also of interest is the fact that the enhanced fluorescence observed from the mixed metals is greater than that observed from the single metal structures. (a) Fluorescein emission from the different metal depositions on glass slides. (b) Enhancement percentage of the different slides relative to a glass control sample.
Figure 10:
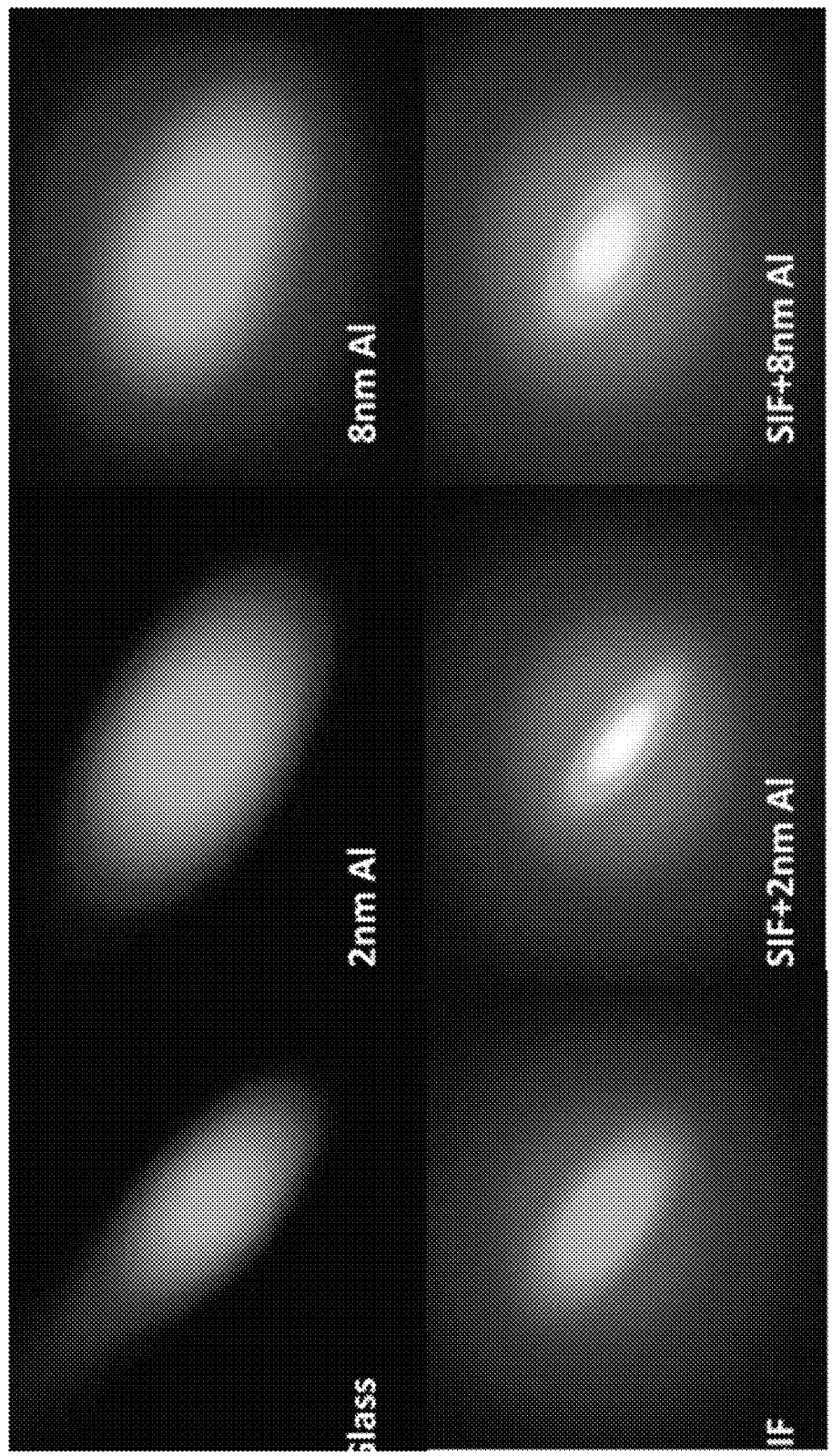
FIG. 10 shows photographs of the actual observed emission from the substrates. The aluminum coated Silver Island Film (SIF) shows the greatest fluorescence enhancement when observed by eye. Excitation was at 473 nm (laser line) and emission was collected through a long pass filter.
Figure 19:
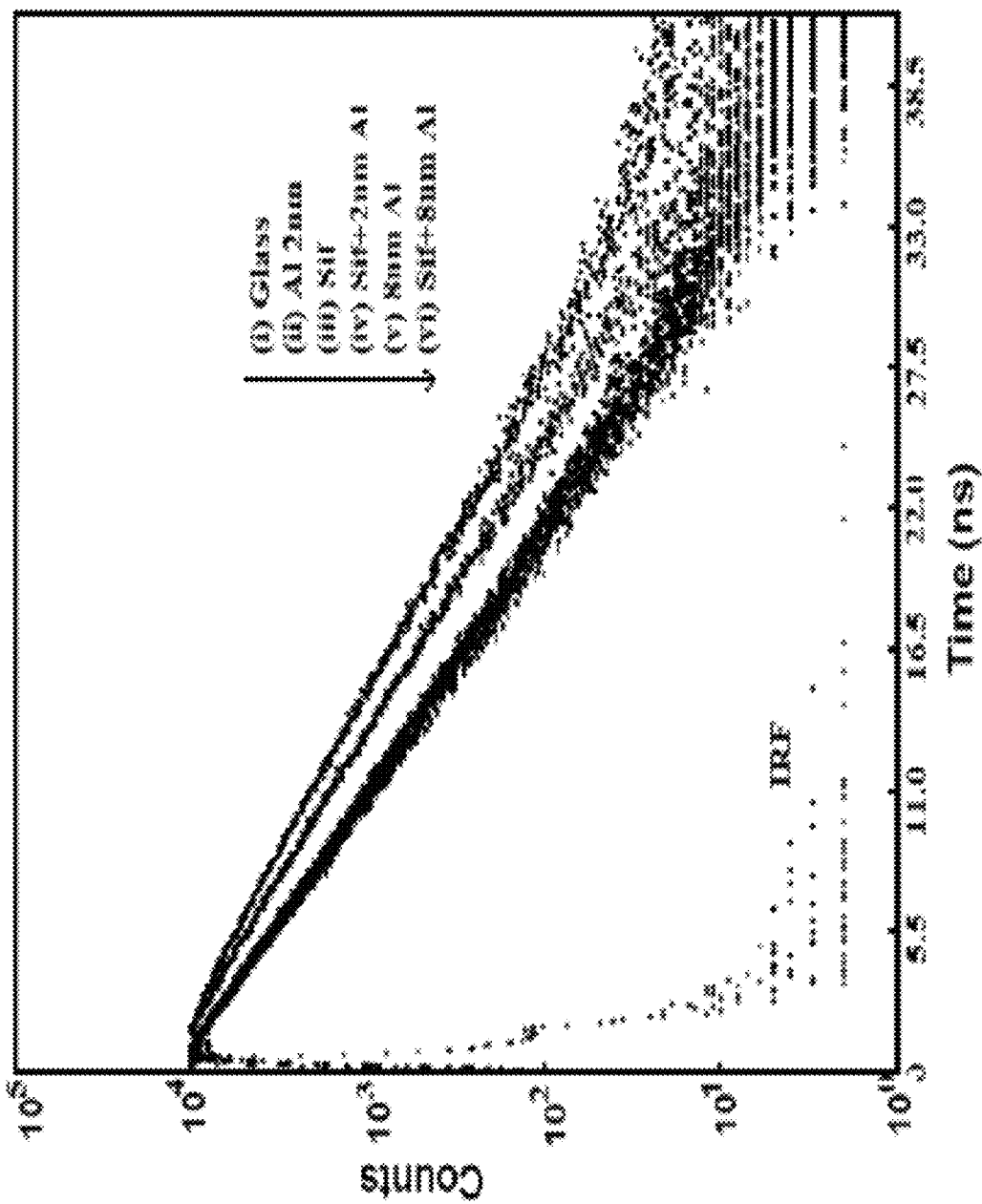
FIG. 19 shows the time-resolved decay curves, the analysis of which is given in Table 1. The mixed metal lifetime can be seen to be the shortest decay, consistent with our thinking and interpretation of the mixed metal concept. Decay curves of Sodium Fluorescein in water [concentration 10-4 µM] from the different metal depositions

To test the utility of the mixed metal substrates for MEF, both traditional and intrinsic fluorescent chromophores were considered, FIG. 9. For a solution of fluorescein sandwiched between the mixed metal substrates and a blank slide, further enhanced luminescence signatures can be seen as compared to the MEF from the individual metals. This finding can also be observed visually in the color photographs of FIG. 10, and suggests that mixed-metal substrates are a much better choice for applications in MEF, as compared to the widely used silver substrates. A similar result as for fluorescein can be seen for Rose Bengal, see FIG. 19.

As briefly mentioned earlier, MEF affords for both enhanced luminescence intensities and reduced fluorophore lifetimes. These observations are empirically underpinned by modifications to the classical far-field (greater than 1 wavelength of light away) rate equations. For a fluorophore in the far-field condition the free-space quantum yield, $Q_0$, is given by:

$$Q_0 = \frac{\Gamma}{\Gamma + K_{nr}} \quad (5)$$

and the fluorescence lifetimes by:

$$\tau_0 = \frac{1}{\Gamma + K_{nr}} \quad (6)$$

where $\Gamma$ is the radiative rate, $\tau_0$ is the free space lifetime and $K_{nr}$ are the non-radiative rates.

In this free-space condition, any changes in a fluorophores' radiative rate, invariably results in the quantum yield and lifetime, $Q_0$ and $\tau_0$ respectively, changing in unison. However for MEF, Geddes has shown that these classical far-field considerations can be rewritten for the near-field condition (3), such that:

$$Q_m = \frac{\Gamma + \Gamma_m}{\Gamma + \Gamma_m + k_{nr}} \quad (7)$$

$$\tau_m = \frac{1}{\Gamma + \Gamma_m + k_{nr}} \quad (8)$$

where $Q_m$ and $t_m$ modified quantum yields and lifetimes respectively.

Figure 20:
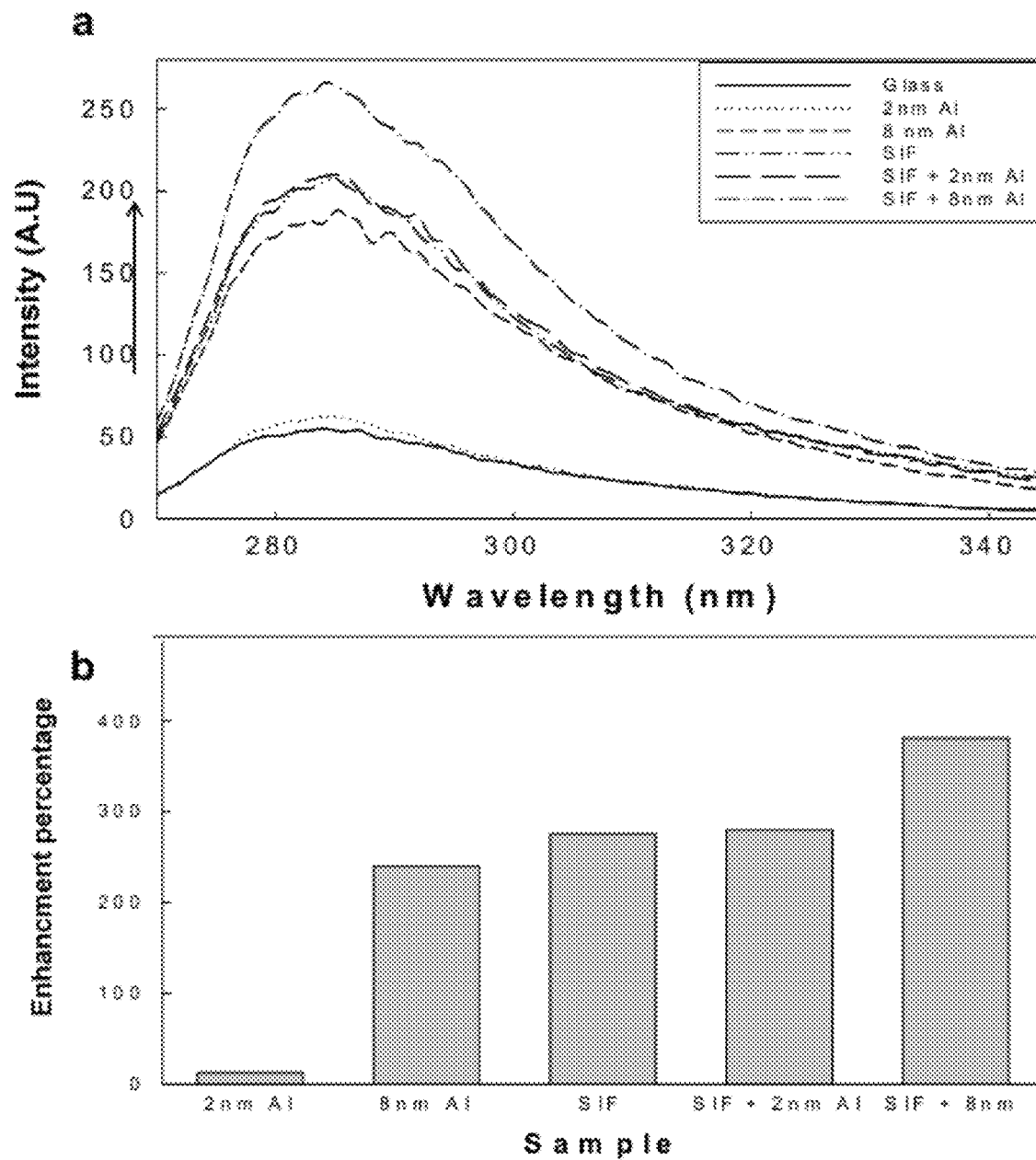
FIG. 20 shows a) Rose-bengal emission from the different depositions on glass slides. b) Enhancement percentage of the different slides relative to a glass control sample. Enhanced emission of the Rose Bengal fluorophore on the single and mixed metal substrates as compared to a glass control sample. As much as a 500% increase can be realized from the Al and SiFs mixed metal substrate.

To test whether mixed-metal substrates follow these near-field approximations, which have been shown to hold for numerous reports of single metals (3; 19), the time-resolved fluorescence decay times were measure, FIG. 20 and Table 1, as shown below. Deconvolution analysis (5) of the decays in FIG. 20, shows the greatest reduction in both amplitude weighted and mean lifetime, Table 1, consistent with the maximum fluorescein fluorescence enhancement shown in FIGS. 9 and 10. This finding is completely consistent with current MEF thinking (4) and equations 7 and 8. From equations 7 and 8, it can be readily seen that an increase in the system radiative rate, $\Gamma_m$, provides for both an enhanced quantum yield, i.e. observed fluorescence intensity along with a reduced decay time (lifetime), consistent with our experimental observations.

TABLE 1

Time resolved decay parameters of Sodium fluorescein in water [concentration 10-4 μM] from the different metal substrates.

| Sample | τ1 | τ2 (ns) | α1 | α2 | τ | <τ> | χ2 |
|---|---|---|---|---|---|---|---|
| 2 nm Al | 5.09 | 2.74 | 0.81 | 0.11 | 4.42 | 4.93 | 0.939 |
| 8 nm Al | 4.42 | 2.23 | 0.95 | 0.05 | 4.31 | 4.36 | 1.180 |
| SIF | 4.46 | 3.13 | 0.65 | 0.34 | 3.96 | 4.11 | 1.082 |
| SIF + 2 nm Al | 4.42 | 2.39 | 0.97 | 0.03 | 4.36 | 4.39 | 1.275 |
| SIF + 8 nm Al | 4.43 | 2.62 | 0.89 | 0.11 | 4.23 | 4.30 | 1.098 |

τ—mean life time, <τ>—is the amplitude life time

Figure 11:
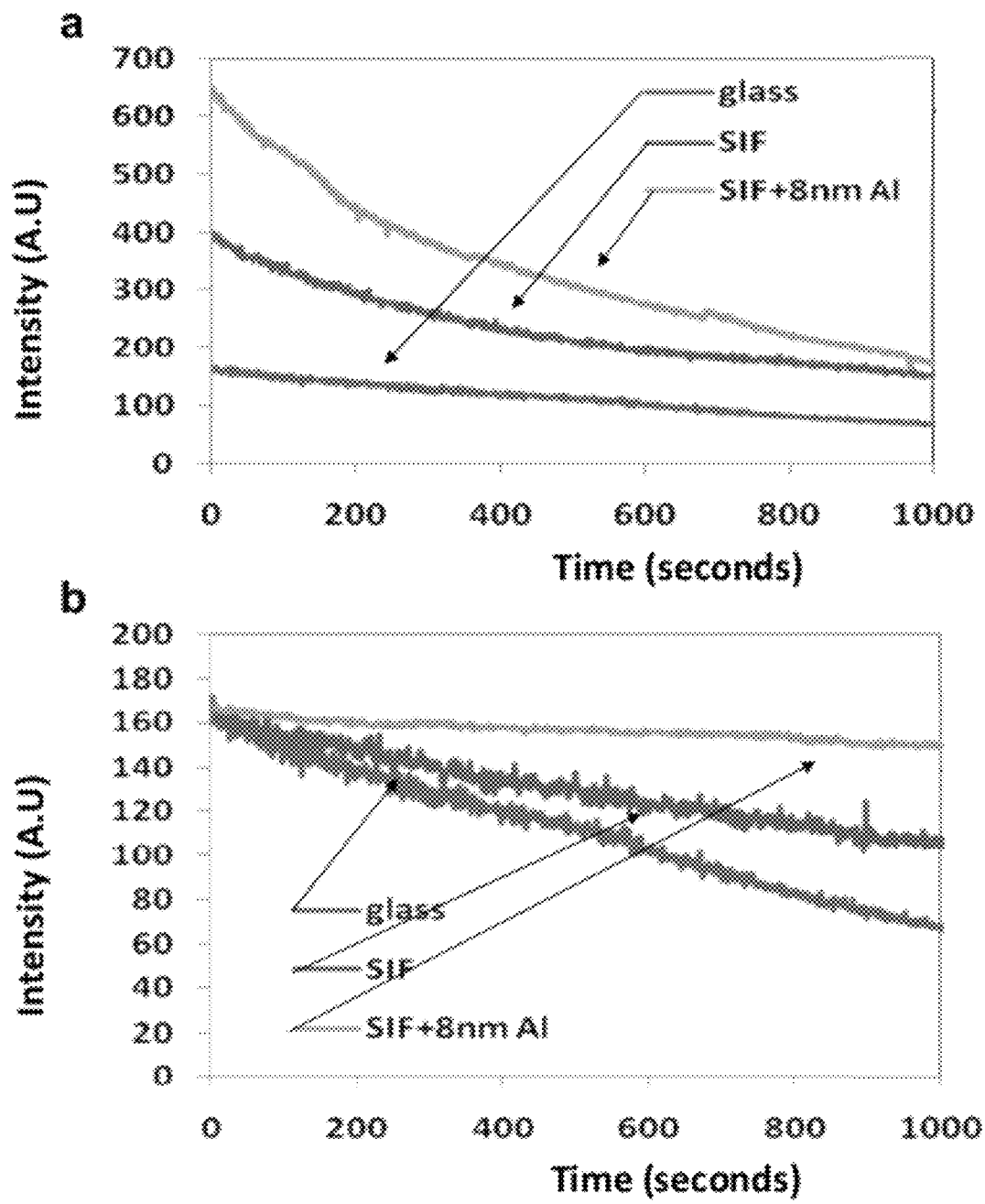
FIG. 11 shows the intensity decay of the fluorescein emission as a function of time, top, where the integrated area under the curves is proportional to the observed photon flux. From this figure it can be seen that the total photon flux is greater from the SiFs and Al deposited surface as compared to SiFs substrate. Interestingly, when the initial steady-state emission intensity was adjusted to match for all samples by adjusting the laser excitation power, it is noted that the photostability of the mixed metal substrate is greater than the other substrates. This observation is also born out in the lifetime data shown in Table 1, where the amplitude weighted lifetimes are shorter on the metalized substrates as compared to the single metals. A molecule with a shorter lifetime often spends less time in an excited state and therefore is less prone to photo oxidation or other processes and hence is more photostable. Intensity decays of fluorescein emission from metal slides (a); and with the initial intensity adjusted to give the same steady state intensity at time T=0 (b).

It is well-known that in classical far-field fluorescence spectroscopy, shorter fluorescence lifetimes are indicative of fluorophores with more enhanced photostabilities, due to these molecules spending less time in highly reactive excited states. Subsequently, the mixed metal substrates using fluorescein were tested. By measuring the steady-state intensity Vs time (i.e. photostability), one typically observes a greater photon flux from the mixed metal substrates, as can be seen in FIG. 11 top, where the photon flux of the sample is proportional to the intergraded area under the respective curves. When the samples are excitation adjusted to reflect the same initial steady-state emission intensity, a further significantly improved photostability can be seen from the mixed-metal substrates. Given that absolute luminescence intensity and photostability is paramount in both microscopy (29) and fluorescence based assays (6), then MMS offer a potentially new solution to this well-recognized old problem.

Mixed-Metal Substrates (MMS) in the UV Spectral Region

Figure 8:
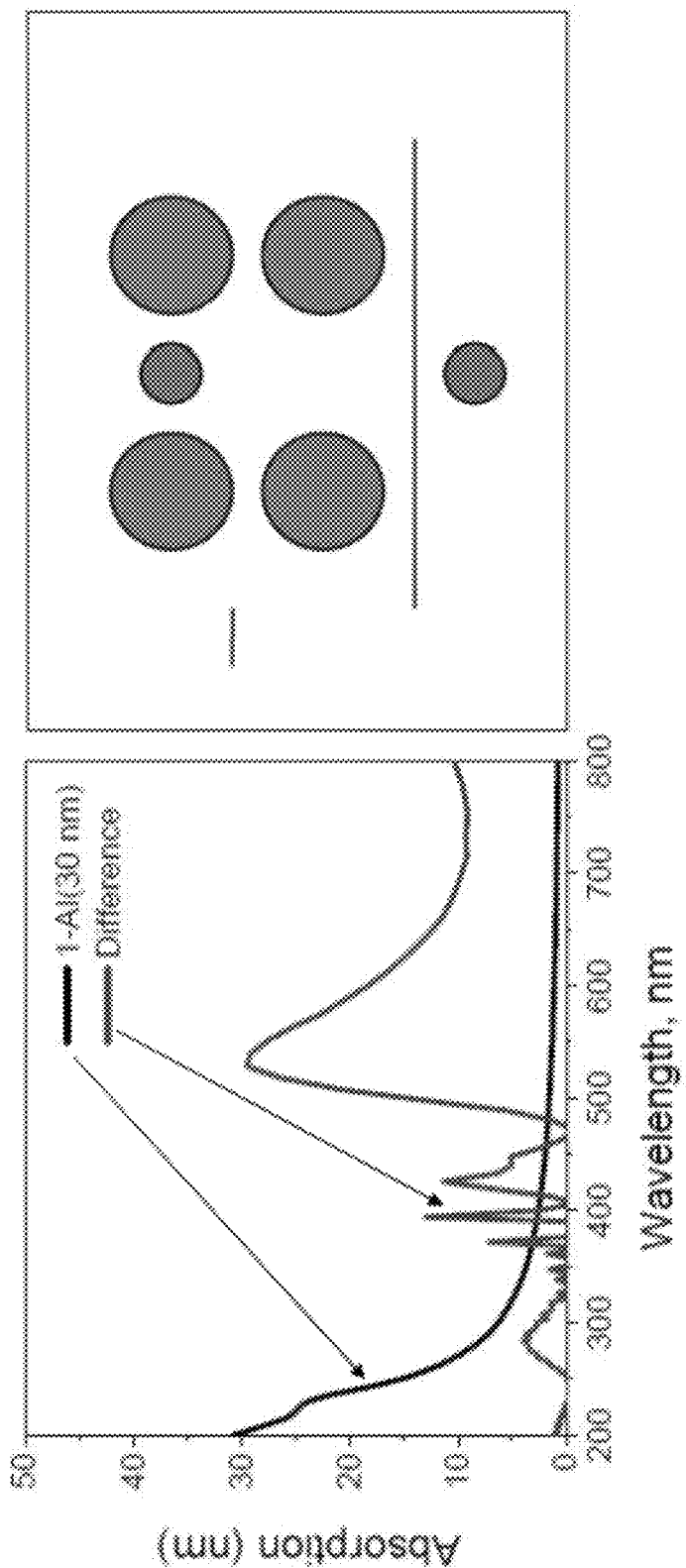
FIG. 8 shows that when an individual spectra is extracted from the combined spectra an extra resonance band appears at around 550 nm. This band is attributed to a plasmon coupled band, a function of the presence of the 2 nanoparticle systems. Interestingly, the measured absorption spectra also show a shift in the spectra as the aluminum is introduced into the mix. Hence, the simulations and experimental data are in agreement. Difference spectra obtained by subtraction of absorption of two silver NPs from the absorption of two silver NPs+the aluminum NP.
Figure 12:
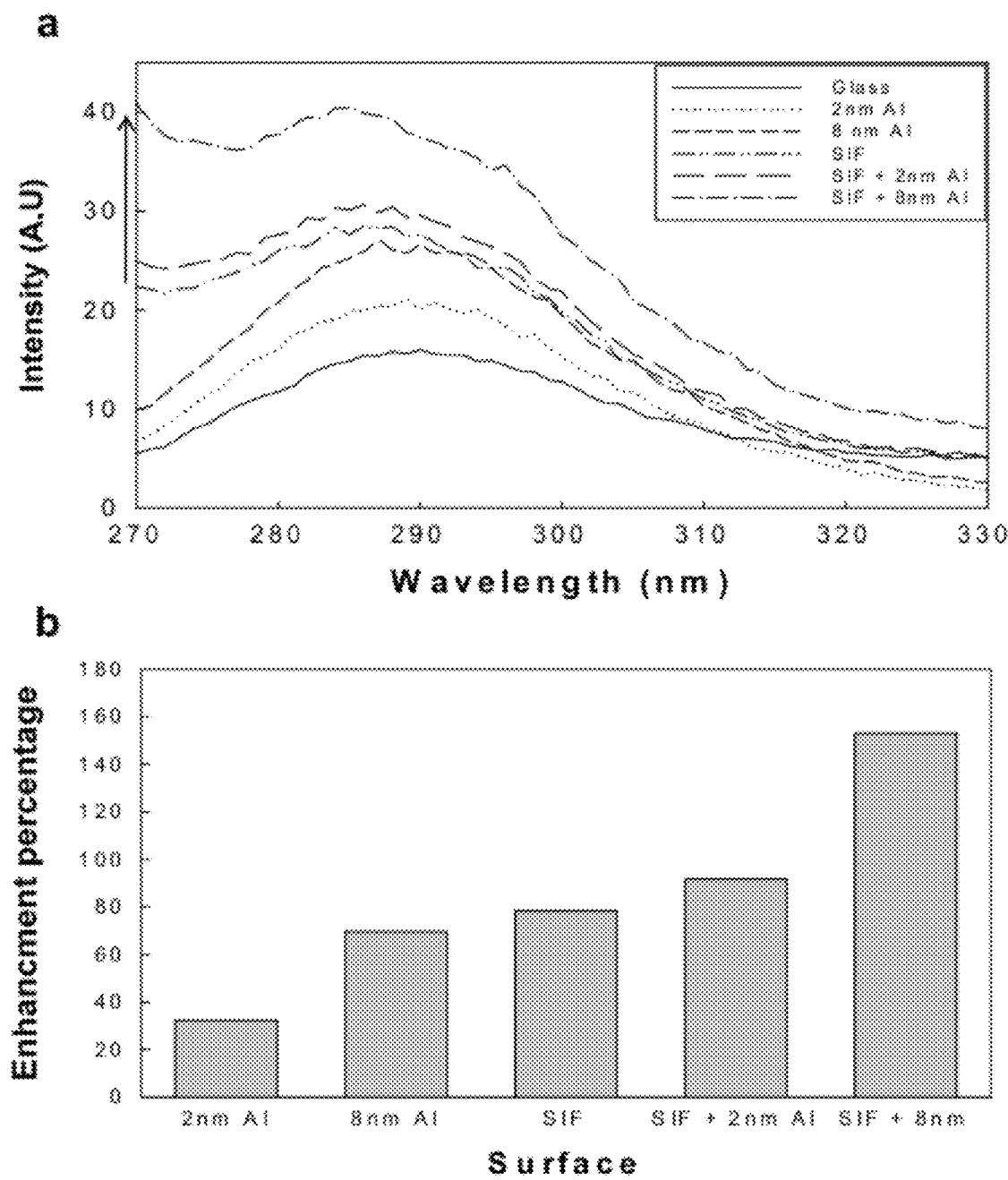
FIG. 12 shows (a) Phenylalanine emission from the different depositions on glass slides. (b) Enhancement percentage from the different slides relative to a glass control sample.
Figure 13:
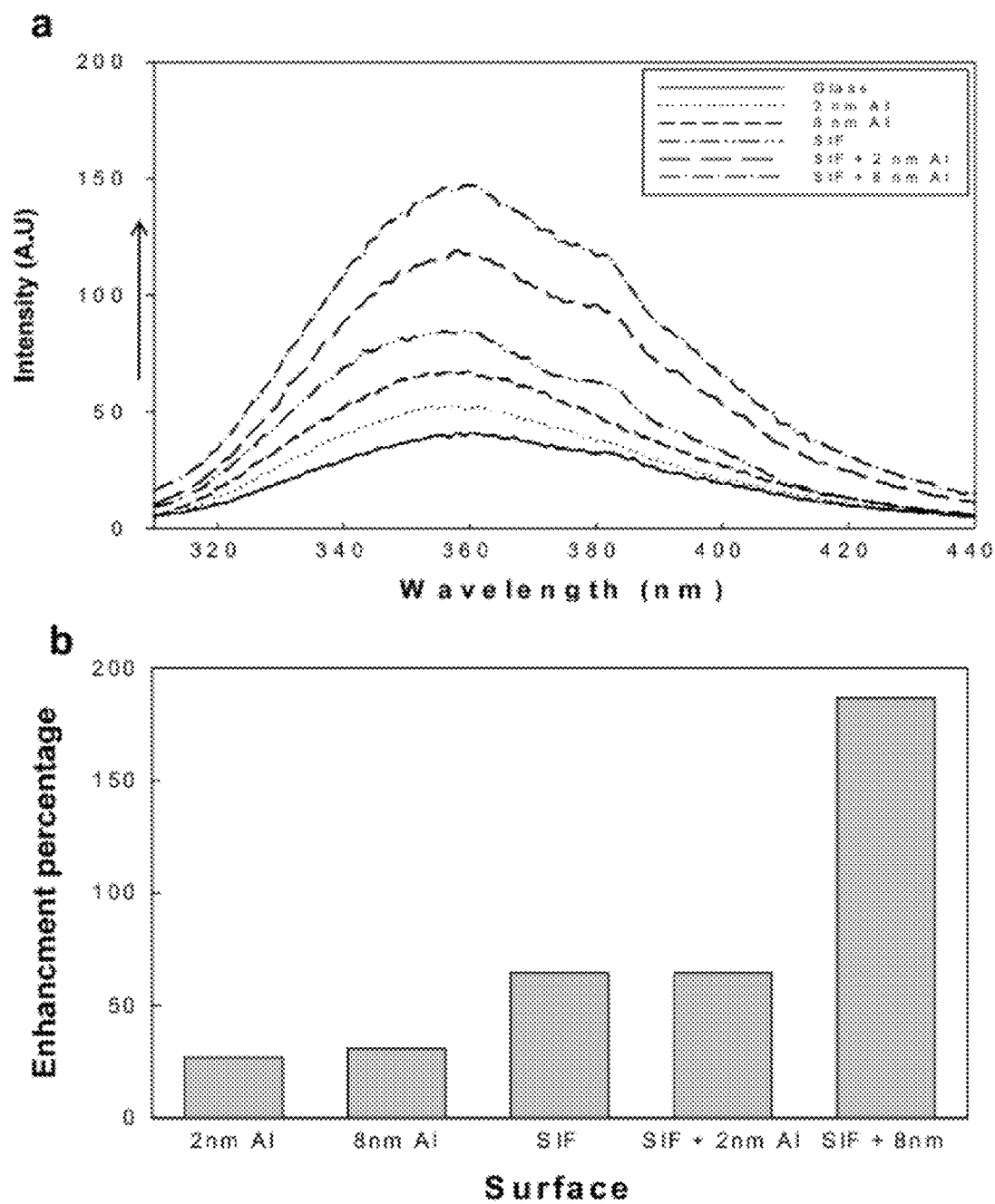
FIG. 13 shows (a) NATA emission from the different depositions on glass slides. (b) Enhancement percentage from the different slides relative to a control glass sample.
Figure 14:
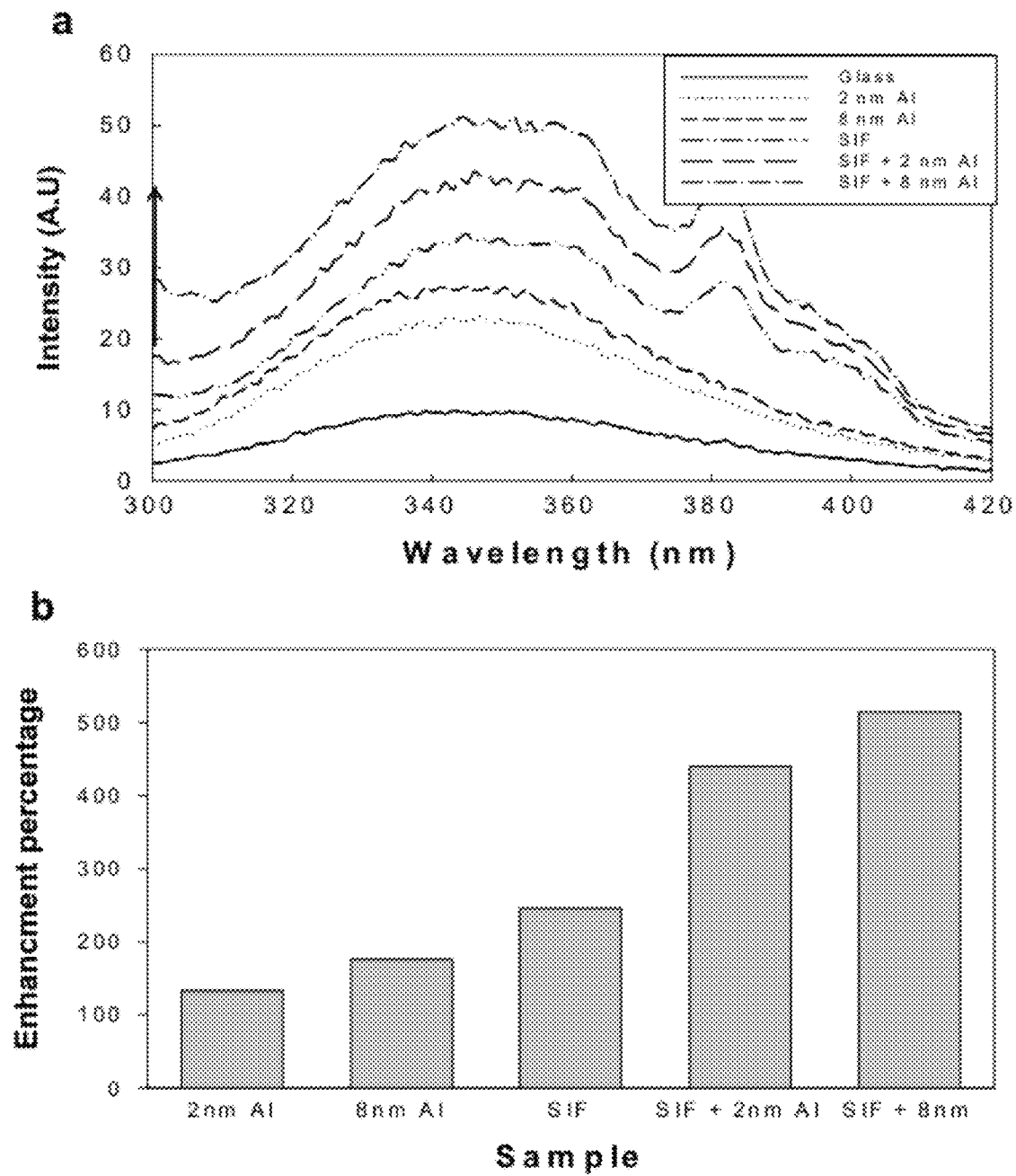
FIG. 14 shows a) BSA emission from the different depositions on glass slides. (b) Enhancement percentage from the different slides relative to a glass control sample. Enhanced emission from BSA demonstrating that intrinsic protein fluorescence can indeed be observed. This finding has utility in understanding protein-protein interactions as well as using the approach for the labeless detection of proteins and other biological materials.

Over the last few years there has been interest in the MEF literature in developing surfaces for MEF in the UV spectral region, particularly for the potential labeless detection of biomolecules, i.e. Metal-Enhanced Fluorescence of intrinsic protein residues, where metals such as Aluminum and Indium have been reported to date (30, 31). To test whether MMS would also enhance UV luminescence labels, solutions of phenylalanine and tryptophan were considered, FIGS. 12 and 13 respectively. Similar to the visible wavelength fluorophores fluorescein and Rose Bengal, MMS also provide for enhanced luminescence of these intrinsic protein residues. Interestingly, solutions of BSA (Bovine Serum Albumin) also show enhanced intrinsic protein luminescence, FIG. 14, with BSA known to contain 21 tyrosine and 3 tryptophan residues (32). Further, it was found that the UV enhancing properties of MMS are more pronounced as compared to the individual metals, as evidenced by the trends in FIGS. 12-14, which could be an effect of the appearance of a new MMS plasmon absorption band, as shown in FIG. 8.

Figure 21:
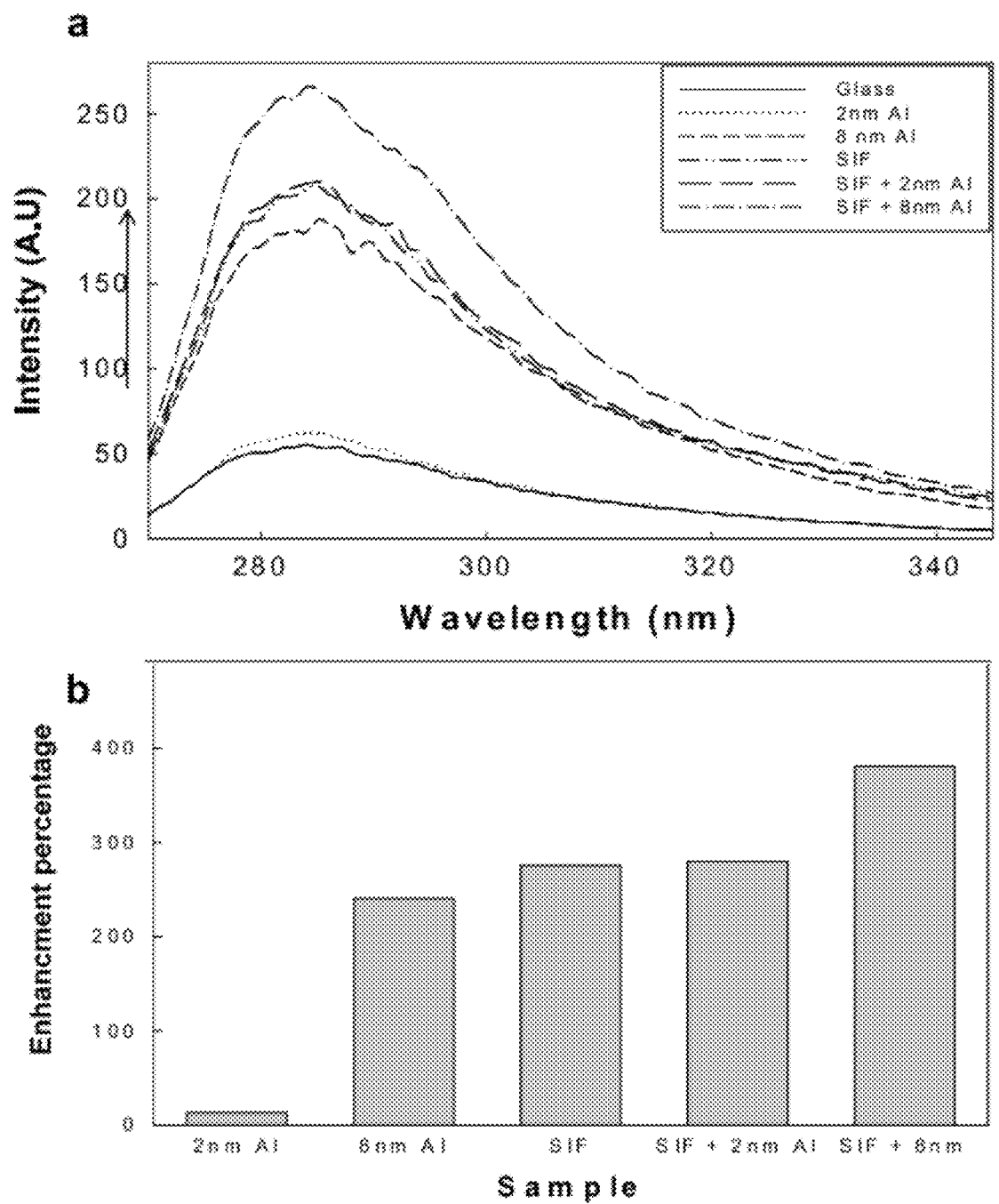
FIG. 21 shows a) Toluene emission from the different depositions on glass slides. b-Enhancement percentage of the different slides relative to a glass control sample; shows enhanced Toluene emission from the mixed metal substrates. Toluene is widely used as the solvent for scintillation counting (radiation detection) and so its enhanced detection may facilitate radiation detection.

FIG. 21 shows that toluene emission is also enhanced on the MMS, suggesting the potential use of MMS in applications such as scintillation counting (33), where solvent emission detectability is a primary concern. In scintillation counting for the detection of radiation such as shown in FIG. 21, the mixed metal surfaces can be used to enhance the emission of toluene which is widely used as a scintillation fluid (often with other solutes). Hence mixed metals, both the substrates as well as nanoparticle mixes, may be new media for the enhanced detection of radiation signatures.

Potential applications of the mixed metal structures can be used for the following:
a) To increase the photostability, brightness and dwell time in microscopy and imaging technologies;
b) On fabrics, textiles and garments for improved visualization, such as safety wear for road side workers or on jogging wear for visualization by traffic;
c) On electronic imaging cameras, such as CCD Cameras, photomultiplier tubes etc.
d) In cosmetics to change the brightness of skin and hair products, for example, Ti improves the photostability of these products and to allow the reduced concentration of dyes/pigments in the formulations;
e) In paints, coatings and inks to enhance brightness as well as protect the material substrates against sun damage;
f) In LCD and plasma screen televisions, to both increase brightness and yet also alter the spatial distribution of luminescence (fluorescence, phosphorescence, chemiluminescence etc);
g) Coated in or on Light Emitting Diodes to increase brightness and the spatial distribution of the emitted light;
h) In bank notes, stock certificates etc as an anti-counterfeiting technology. The angular nature and enhanced luminescence signatures can not be simply duplicated by simple printing or photocopying;
i) In the generation of solar cells using the plasmonic electricity concept disclosed herein allows for tunable electric currents to be realized, not achievable using a single metal substrate.
j) In a contact lens embodiment to change the spatial distribution of light passing through the lens as well as to change the cosmetic color of the lens;
k) On and with fiber optics and optical cables to enhance luminescence signatures, increase the extent of light coupling into the fiber as well as increase and tune the extent the magnitude of the evanescent wave above and at the end of the fibers;
l) To modify plasmon modes in metallic substrates, particles, thin and thick films;
m) For the generation of singlet oxygen, $^1O_2$, near-to the substrates or near-to the 3D embodiment of the technology, i.e. mixed metal nanoballs. Applications include photodynamic therapy and sterilization, disinfection;
n) For the enhanced generation of superoxide anion radicals, near-to the substrates or near-to the 3D embodiment of the technology, i.e. mixed metal nanoballs, for applications such as in sterilization or disinfection of harmful bacteria such as MRSA, *salmonella*, STDs, Anthrax spores etc;
o) For use enhancing the luminescence of ds-DNA sensing probes such as picogreen, ethidium bromide and cyber green to name a few;
p) As a substrate for the enhanced detection of analytes, using fluorophores sensitive to such analytes such as Iodide, chlorine, bromine, Calcium, Zinc, Lithium, Copper, and any other element on the period table, ions and compounds thereof;
q) For use as a surface in voltage-gated immunoassays;
r) As a substrate for the enhanced detection of e-type or delayed fluorescence;
s) As a substrate for the enhanced detection of $S_2$ or other higher excited singlet or triplet states;
t) As a substrate for the enhanced detection of P-type fluorescence, such as assays using the pyrene chromophore; and
u) As a coating to enhance the throughput of emission in surface plasmon coupled fluorescence (SPCF) and surface plasmon coupled emission (SPCE) applications.

REFERENCES

The contents of all references are incorporated by reference herein for all purposes.
1. D'Agostino, S., Pompa, P. P., Chiuri, R., Phaneuf, R. J., Britti, D. G., Rinaldi, R., Cingolani, R., and Della Sala, F. (2009) Enhanced fluorescence by metal nanospheres on metal substrates, *Opt. Lett.* 34, 2381-2383.
2. Dragan, A. I., Bishop, E. S., Casas-Finet, J. R., Strouse, R. J., Schenerman, M. A., and Geddes, C. D. (2010) Metal-enhanced PicoGreen fluorescence: Application for double-stranded DNA quantification, *Anal. Biochem.* 396, 8-12.
3. Geddes, C. D. and Lakowicz, J. R. (2002) Metal-enhanced fluorescence, *Journal of Fluorescence* 12, 121-129.

4. Geddes, C. D. (2010) *Metal-Enhanced Fluorescence* John Willey & sons, Inc., Hoboken, N.J.
5. Lakowicz, J. R. (2006) *Principles of fluorescence spectroscopy* Springer Science+Business Media, LLC, New York.
6. Asian, K., Gryczynski, I., Malicka, J., Matveeva, E., Lakowicz, J. R., and Geddes, C. D. (2005) Metal-enhanced fluorescence: an emerging tool in biotechnology, *Current Opinion in Biotechnology* 16, 55-62.
7. Asian, K., Previte, M. J. R., Zhang, Y. X., Gallagher, T., Baillie, L., and Geddes, C. D. (2008) Extraction and detection of DNA from *Bacillus anthracis* spores and the vegetative cells within 1 min, *Analytical Chemistry* 80, 4125-4132.
8. Mackowski, S., Wormke, S., Maier, A. J., Brotosudarmo, T. H., Harutyunyan, H., Hartschuh, A., Govorov, A. O., Scheer, H., and Brauchle, C. (2008) Metal-enhanced fluorescence of chlorophylls in single light-harvesting complexes, *Nano. Lett.* 8, 558-564.
9. Matveeva, E. G., Gryczynski, I., Barnett, A., Leonenko, Z., Lakowicz, J. R., and Gryczynski, Z. (2007) Metal particle-enhanced fluorescent immunoassays on metal mirrors, *Analytical Biochemistry* 363, 239-245.
10. Drexhage, K. H. (1970) Influence of a dielectric interface on fluorescence decay time., *J. Lumin* 1, 693-701.
11. Persson, B. N.J. (1978) Theory of dumping of excited molecules located above a metalic-surface., *J. Phys. C Solid State Phys* 4251-4269.
12. Chowdhury, M. H., Asian, K., Malyn, S, N., Lakowicz, J. R., and Geddes, C. D. (2006) Metal-enhanced chemiluminescence, *Journal of Fluorescence* 16, 295-299.
13. Zhang, Y. X., Asian, K., Previte, M. J. R., Malyn, S, N., and Geddes, C. D. (2006) Metal-enhanced phosphorescence: Interpretation in terms of triplet-coupled radiating plasmons, *Journal of Physical Chemistry B* 110, 25108-25114.
14. Zhang, Y. X., Asian, K., Previte, M. J. R., and Geddes, C. D. (2007) Metal-enhanced singlet oxygen generation: A consequence of plasmon enhanced triplet yields, *Journal of Fluorescence* 17, 345-349.
15. Zhang, Y. X., Asian, K., Previte, M. J. R., and Geddes, C. D. (2007) Metal-enhanced superoxide generation: A consequence of plasmon-enhanced triplet yields, *Applied Physics Letters* 91.
16. Zhang, Y., Dragan, A., and Geddes, C. D. (2009) Wavelength Dependence of Metal-Enhanced Fluorescence, *Journal of Physical Chemistry C* 113, 12095-12100.
17. Asian, K., Malyn, S, N., and Geddes, C. D. (2008) Angular-dependent metal-enhanced fluorescence from silver island films, *Chemical Physics Letters* 453, 222-228.
18. Dragan, A. I., Bishop, E. S., Casas-Finet, J. R., Strouse, R. J., McGivney, J., Schenerman, M. A., and Geddes, C. D. (2010) Distance dependence of metal-enhanced fluorescence, *Journal of the American Chemical Society Submitted*.
19. Ray, K., Badugu, R., and Lakowicz, J. R. (2006) Distance-dependent metal-enhanced fluorescence from Langmuir-Blodgett monolayers of alkyl-NBD derivatives on silver island films, *Langmuir* 22, 8374-8378.
20. Dragan, A. I. and Geddes, C. D. (2010) Excitation Volumetric Effects (EVE) in Metal-Enhanced Fluorescence., *Journal of the American Chemical Society Submitted*.
21. Aslan, K. and Geddes, C. D. (2010) Metal-enhanced fluorescence: progress towards a unified plasmon-fluorophore description., in *Metal-enhanced fluorescence*. (Geddes, C. D., Ed.) pp 1-24, John Wiley & Sons, Inc., Hoboken, N.J.
22. Chowdhury, S., Bhethanabotla, V. R., and Sen, R. (2009) Silver-copper alloy nanoparticles for metal enhanced luminescence, *Applied Physics Letters* 95.
23. Zhang, Y., Mandeng, L. N., Bondre, N., Dragan, A., and Geddes, C. D. (2010) Metal-enhanced fluorescence from silver-SiO2-silver nanoburger structures, *Langmuir* 26, 12371-12376.
24. Lal, S., Grady, N. K., Kundu, J., Levin, C. S., Lassiter, J. B., and Halas, N.J. (2008) Tailoring plasmonic substrates for surface enhanced spectroscopies, *Chemical Society Reviews* 37, 898-911.
25. Wang, H., Brandi, D. W., Nordlander, P., and Halas, N.J. (2007) Plasmonic nanostructures: Artificial molecules, *Accounts of Chemical Research* 40, 53-62.
26. Burstein, E. A. (1977) *Intrinsic luminescence of proteins* VINITI, Academy of Science, USSR, Moscow.
27. Demchenko, A. P. (1981) *Ultraviolet spectroscopy of proteins* Springer-Verlag, New York.
28. Pribik, R., Dragan, A. I., Zhang, Y., Gaydos, C., and Geddes, C. D. (2009) Metal-Enhanced Fluorescence (MEF): Physical characterization of Silver-island films and exploring sample geometries, *Chemical Physics Letters* 478, 70-74.
29. Phan, T. G. and Bullen, A. (2010) Practical intravital two-photon microscopy for immunological research: faster, brighter, deeper, *Immunology and Cell Biology* 88, 438-444.
30. Chowdhury, M. H., Ray, K., Gray, S. K., Pond, J., and Lakowicz, J. R. (2009) Aluminum nanoparticles as substrates for metal-enhanced fluorescence in the ultraviolet for the label-free detection of biomolecules, *Anal. Chem.* 81, 1397-1403.
31. Dragan, A. I. and Geddes, C. D. (2010) Indium nanodeposits: A substrate for Metal-Enhanced Fluorescence in the UV spectral region, *Journal of Applied Physics Submitted*.
32. Hirayama, K., Akashi, S., Furuya, M., and Fukuhara, K. (1990) Rapid confirmation and revision of the primary structure of bovine serum albumin by ESIMS and Frit-FAB LC/MS, *Biochem. Biophys. Res. Commun.* 173, 639-646.
33. Wilkinson, D. H. (1974) *Applications of liquid scintillation counting* North Holland, Amsterdam.

That which is claimed is:
1. A detection system, the system comprising:
a multiplicity of metallic structures, wherein the metallic structures are metallic particles having a geometric shape selected from the group consisting of a sphere, triangle, square, oblong, elliptical and rectangle and wherein the metallic particles are separated from each other at a distance of 40 to 50 nm, wherein each of the metallic particles comprises mixed-metals and are fabricated from a combination of two plasmon supporting metals wherein the two plasmon supporting metals comprise a silver metallic particle having a coating from about 2 nm to about 8 nm of aluminum deposited thereon, wherein the metallic structures further comprise a capture probe having affinity for a target molecule in a sample used in the detection system, wherein the two plasmon supporting metals provide an additional plasmon resonance band not present in the plasmon absorption spectra of either silver or aluminum, wherein the metallic structures are immobilized on a substrate and the substrate is selected from the group consisting of glass, quartz, polymeric materials, and cellulose;

at least one excitable molecule that is positioned near the multiplicity of metallic structures in a range from about 5 nm to 30 nm from the multiplicity of metallic structures, wherein the excitable molecule is selected from the group of an intrinsic fluorophore, extrinsic fluorophore, fluorescent dye, a luminophore, a chemiluminescent species and a bioluminescent species and wherein the excitable molecule is attached to a free probe and wherein the binding of the free probe to the target molecule causes the excitable molecule to be positioned from about 5 nm to 30 nm from the multiplicity of metallic structures;

a source of electromagnetic energy for exciting the excitable molecule if the excitable molecule is an intrinsic fluorophore, extrinsic fluorophore, fluorescent dye or a luminophore; and a detector for detecting emissions from the excited molecule and/or the metallic structures.

2. The detection system according to claim 1, wherein the intrinsic fluorophore is a protein.

3. The detection system according to claim 1, wherein the excitable molecule emits a detectable signal upon excitation and when positioned from 5 nm to 20 nm from the metallic structures.

4. The detection system according to claim 1, wherein the excitable molecule comprises a first and second component of a bioluminescence or chemiluminescence generating system.

5. A method for detecting emissions from an excitable molecule in a detection system, the method comprising:

providing a substrate comprising a multiplicity of metallic structures, wherein the metallic structures are metallic particles having a geometric shape selected from the group consisting of a sphere, triangle, square, oblong, elliptical and rectangle and wherein the metallic particles are separated from each other at a distance of 40 to 50 nm wherein each of the metallic particles comprises mixed-metals, wherein the metallic structures are fabricated from a combination of two plasmon supporting metals wherein the two plasmon supporting metals consist of a silver metallic particle having a coating from about 2 nm to about 8 nm of aluminum deposited thereon, wherein the metallic structures have positioned thereon a receptor molecule having affinity for a ligand of interest in a sample, wherein the ligand of interest binds to the receptor molecule to form a receptor-ligand complex and the excitable molecule binds to the receptor-ligand complex, wherein the at least two plasmon supporting metals provide an additional plasmon resonance band not present in the plasmon absorption spectra of either silver or aluminum, wherein the metallic structures are immobilized on a substrate and the substrate is selected from the group consisting of glass, quartz, polymeric materials, and cellulose;

positioning the excitable molecule near the multiplicity of metallic structures in a range from about 5 nm to 30 nm from the multiplicity of metallic structures, wherein the excitable molecule is selected from the group of an intrinsic fluorophore, extrinsic fluorophore, fluorescent dye, a luminophore, a chemiluminescent species and a bioluminescent species;

applying electromagnetic energy for exciting the excitable molecule if the excitable molecule is an intrinsic fluorophore, extrinsic fluorophore, fluorescent dye or a luminophore; and detecting emissions from the excited molecule and/or the metallic structures.

\* \* \* \* \*